US006269818B1

(12) United States Patent
Lui et al.

(10) Patent No.: US 6,269,818 B1
(45) Date of Patent: Aug. 7, 2001

(54) PHOTOACTIVATION OF ENDOGENOUS PORPHYRINS FOR TREATMENT OF PSORIASIS

(75) Inventors: Harvey Lui; Calum Macaulay, both of Vancouver; Haishan Zeng, Delta; David I. McLean; Robert Bissonnette, both of Vancouver, all of (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/084,865

(22) Filed: May 26, 1998

(51) Int. Cl.⁷ ..................................................... A61B 19/00
(52) U.S. Cl. .................................. 128/898; 606/1; 607/88
(58) Field of Search ..................... 606/1, 3, 9, 10, 606/11, 12, 14, 16, 17; 607/88, 89; 128/898

(56) References Cited

U.S. PATENT DOCUMENTS

| 5,079,262 |   | 1/1992 | Kennedy et al. . |         |
|-----------|---|--------|------------------|---------|
| 5,211,938 |   | 5/1993 | Kennedy et al. . |         |
| 5,234,940 |   | 8/1993 | Kennedy et al. . |         |
| 5,405,957 | * | 4/1995 | Tang et al. ............................ | 540/472 |
| 5,422,093 |   | 6/1995 | Kennedy et al. . |         |

(List continued on next page.)

FOREIGN PATENT DOCUMENTS

| 96/06602 | 3/1996 | (WO) . |
| 96/09853 | 4/1996 | (WO) . |

OTHER PUBLICATIONS

Policard, A., "Etude sur les aspects offerts par des tumeurs experimentales examinees a la lumiere de Wood," *Comptes Rendus de la Societe de Biologie*, 91:423–424 (1924).

Gougerot et al. "Fluorescence des epitheliomas a la lumiere de Wood," *Bulletin de la Societe Francaise de Dermatologie et de Syphiligraphie*, 46:228–295 (1939).

Ronchese, F., "The Fluorescence of Cancer under the Wood's Light," *Oral Surg. Med. Oral Pathol.* 7:967–971 (1954).

Ghadially et al., "Porphyrin Fluorescence of Experimentally Produced Squamous Cell Carcinoma," *Nature* 188:1124–1125.

Pathak et al., "The Porphyrin Content of Skin," *J. Investigative Dermatology*, 43:119–120 (1964).

Cornelius et al., "Red Fluorescence of Comedones: Production of Porphyrins by Corynebacterium Acne," *J. Invest. Derma.* 49:368–370 (1967).

(List continued on next page.)

*Primary Examiner*—Michael Peffley
*Assistant Examiner*—R. Kearney
(74) *Attorney, Agent, or Firm*—Townsend and Townsend and Crew LLP

(57) ABSTRACT

In one aspect, the invention provides a diagnostic method for identifying psoriatic plaques in which Porphyrins, particularly protoporphyrin IX, are elevated as compared to normal skin and skin of patients with other dermatological diseases, including other forms of psoriatic plaque. Psoriatic plaques with elevated porphyrin levels may be detected by fluorescence and spectral analysis. Endogenous porphyrins in psoriatic plaques may be activated with visible light to treat psoriatic plaques having elevated porphyrin concentrations. Skin conditions may be optimized to increase the endogenous concentration of porphyrins in psoriatic plaques. A topical formulation may be applied to psoriatic plaques to optimize skin conditions such as pH, iron concentration, temperature, hydration, calcium concentration, oxygenation, electrical conductivity and estrogen concentration to increase the concentration of endogenous porphyrins.

19 Claims, 11 Drawing Sheets

U.S. PATENT DOCUMENTS

| | | |
|---|---|---|
| 5,438,051 | 8/1995 | Morgan et al. . |
| 5,512,675 * | 4/1996 | Tang et al. ............................ 540/472 |
| 5,520,905 | 5/1996 | Uhlmann et al. . |
| 5,556,612 * | 9/1996 | Anderson et al. . |
| 5,563,132 | 10/1996 | Bodaness . |
| 5,726,304 * | 3/1998 | Tang et al. ............................ 540/145 |
| 5,945,439 * | 8/1999 | Richter et al. ........................ 514/410 |

OTHER PUBLICATIONS van Gog et al., "Determination of Very Small Amounts of Protoporphyrin in Epidermis, Plasma, and Blister Fluids," *J. Invest. Derma.* 61:42–45 (1973).

Lee et al., "Comparative Studies of porphyrin Production in *Propionibacterium acnes* and *Propionibacterium granulosum,*" *J. Bacteriology* 133:811–815 (1978).

Malina et al., "Skin Porphyrin Assay in Porphyria," *Clinica Chimica Acta* 83:55–59 (1978).

McGinley et al., "Facial Follicular Porphyrin Fluorescence: Correlation with Age and Density of *Propionibacterium acnes,*" *J. Dermatol.* 102:437–441 (1980).

Kjeldstad et al., "Influence of pH on Porphyrin Production in *Propionibacterium acnes,*" *Arch. Dermatol. Res.*, 276:396–400 (1984).

Nelson et al., "Topical 5–aminolevulinic acid (ALA) for the Photodynamic Therapy of Psoriasis and Actinic Keratoses," *Am. Soc. Laser Med. Surg.* (Abstract) p. 43, No. 202 (1985).

Brault et al., "Spectrofluorimetric Study of Porphyrin Incorporation into Membrane Models—Evidence for pH Effects," *Biochimica et Biophysica ACTA* 857:238–250 (1986).

Rosenthal et al., "The Role of Molecular Oxygen in the Photodynamic Effect of Phthalocyanines," *Radiation Res.* 107:136–142 (1986).

Johnsson et al., "Fluorescence from Pilosebaceous Follicles," *Arch. Dermatol. Res.* 279:190–193 (1987).

Harris et al., "Endogenous Porphyrin Fluorescence in Tumors," *Lasers in Surgery and Medicine*, 7:467–472 (1987).

Thomas and Girotti, "Glucose Administration Augments in vivo Uptake and Phototoxicity of the Tumor–Localizing Fraction of Hematoporphyrin Derivative," *Photochem. Photobiol.* 49:241–247 (1989).

Kennedy et al., "Photodynamic Therapy Protoporphyrin IX: Basic Principles and Experience," *J. Photochem Photobiol.* 6:143–148 (1990).

Gottfried et al., "Temperature Effects on Photosensitized Processes," *J. Photochem Photobiol.* 8:419–30 (Abstract) (1991).

Chapman et al., "Oxygen Dependency of Tumor Cell Killing in Vitro by Light–Activation Photofrin II," *Radiation Res.* 126:73–79 (1991).

Hanania et al., "The Effect of EDTA and Serum on Endogenous Porphyrin Accumulation and Photodynamic Sensitization of Human K562 Lukemic Cells," *Cancer Letters*, 65:127–131 (1992).

Nelson et al., "Glucose Administration Combined with Photodynamic Therapy of Cancer Improves Therapeutic Efficacy," *Lasers in Surgery and Medicine* 12:153–158 (1992).

Konig et al., "Fluorescence Detection and Photodynamic Activity of Endogenous Protoporphyrin in Human Skin," *Optical Engineering* 31:1470–1474 (1992).

Rebeiz et al., "Photodestruction of Tumor Cells by Induction of Endogenous Accumulation of Protoporphyrin IX: Enhancement by 1,10–Phenanthroline," *Photochem. Photobiol.* 55:431–435 (1992).

Penning et al., "A Role for the Transient Increase of Cytoplasmic Free Calcium in Cell Rescue after Photodynamic Treatment," *Biochimica et Biophysica Acta* 1107:255–260 (1992).

Ben–Hur, E., "Cytoplasmic Free Calcium Changes as a Trigger Mechanism in the Response of Cells to Photosensitization," *Photochemistry and Photobiology* 58:890–894 (1993).

Zeng et al., "Laser–Induced Changes in Autofluorescence of in vivo Skin," *SPIE Laser–Tissue Interaction IV*, 1882:278–290 (1993).

Zeng et al., "Novel Microspectrophotometer and its Biomedical Applications," *Optical Engineering* 32:1809–1814 (1993).

Boehncke et al., Treatment of Psoriasis by Topical Photodynamic Therapy with Polychromatic Light (letter), *Lancet* 343:801 (1994).

Konig et al., "In vivo Fluorescence Detection and Imaging of Porphyrin–Producing Bacteria in the Human Skin and in the Oral Cavity for Diagnosis of Acne Vulgaris, Caries and Squamous Cell Carcinoma," *SPIE* 2135:129–138 (1994).

Richelli et al., "Temperature–Induced Changes in Fluorescence Properties as a Probe of Porphyrin Microenvironment in Lipid Membranes, 1. The Partition of Hematoporphyrin and Protoporphyrin in Liposomes," *Eur. J. Biochem.* 233:159–164 (1995).

Richelli et al., "Temperature–Induced Changes in Fluorescence Properties as a Probe of Porphyrin Microenvironment in Lipid Membranes, 2. The Partition of Hematoporphyrin and Protoporphyrin in Mitochondria," *Eur. J. Biochem.* 233:159–164 (1995).

Goerz et al., "Porphyrin Concentrations in Various Human Tissues," *Exp. Dermatol.* 4:218–220 (1995).

Zeng et al., "Spectroscopic and Microscopic Characteristics of Human Skin Autofluorescence Emission," *J. Photochem. Photobiol.* 61:639–645 (1995).

Berg et al., "The Influence of Iron Chelators on the Accumulation of Protoporphyrin IX in 5–aminolaevulinic Acid–treated Cells," *Br. J. Cancer* 74:688–697 (1996).

Alfano and Katz, "Photonic Pathology: Fluorescence and Raman Spectroscopy for Tissue Diagnosis and Characterization," *Analytical Use of Fluorescent Probes in Oncology*, Plenum Press, NY (1996).

Arakane et al., "Singlet Oxygen ($^1\Delta_g$) Generation from Coproporphyrin in Propionibacterium acnes on Irradiation," *Biochem. Biophys. Res. Comm.* 578–582 (1996).

Peng et al., "Build –up of Esterified Aminolevulinic–acid–derivative–induced Porphyrin Fluorescence in Normal Mouse Skin," *J. Photochem. Photobiol.*, 34:95–96 (1996).

Dhingra et al., "Early Diagnosis of Upper Aerodigestive Tract Cancer by Autofluorescence," *Arch Otolaryngol. Head Neck Surg.* 122:1181 (Nov. 1996).

Lucchina et al., "Fluorescence Photography in the Evaluation of Acne," *J. Am. Acad. Dermatol.* 35:58–63 (1996).

Stringer et al., "The Accumulation of Protoporphyrin IX in Plaque Psoriasis after Topical Application of 5–Aminolevulinic Acid Indicates a Potential for Superficial Photodynamic Therapy," *J. Invest. Dermatol.* 107:76–81 (1996).

Szeimies et al., "Topical Photodynamic Therapy in Dermatology," *J. Photochem. Photobiol.* 36:213–219 (1996).

Tan et al., "Enhancement of Photodynamic Therapy in Gastric Cancer Cells by Removal of Iron," Gut 41:14–18 (1997).

Rick et al., "Pharmaokinetics of 5–aminolevulinic Acid–Induced Protoporphyrin IX in Skin and Blood," J. Photochem. Photobiol. 40:313–319 (1997).

Ochsner, M., "Photophysical and Photobiological Processes in the Photodynamic Therapy of Tumours," J. Photochem. Photobiol., 39:1–18 (1997).

Beck et al., "A Hydroxypyridinone (CP94) Enhances Protoporphyrin IX Formation in 5–aminolaevulinic Acid Treated Cells," J. Photochem. Photobiol. 41:136–144 (1997).

Bech et al., "The pH Dependency of Protoporphyrin IX Formation in Cells Incubated with 5–aminolevulinic Acid," Cancer Letters 113:25–9 (Abstract) (1997).

Chang et al., "The Efficacy of an Iron Chelator (CP94) in Increasing Cellular Protoporphyrin IX Following Intravesical 5–aminolaevulinic Acid Administration: an In Vivo Study," J. Photochem. Photobiol. 38:114–122 (1997).

Collins et al., "The Variable Response of Plaque Psoriasis after a Single Treatment with Topical 5–aminolaevulinic Acid Photodynamic Therapy," Br. J. Derma. 137:743–749 (1997).

Fuchs et al., "pH–Dependent Formation of 5–aminolaevulinic Acid–Induced Protoporphyrin IX in Fibrosarcoma Cells," J. Photochem. Photobiol., 40:49–54 (1997).

Ingrams et al., "Autofluorescence Characteristics of Oral Mucosa," Head & Neck 27–32 (Jan., 1997).

Strauss et al., "Photodynamic Efficacy of Naturally Occurring Porphyrins in Endothelial Cells in vitro and Microvasculature in vivo," J. Photochem. Photobiol. 39:176–184 (1997).

Moan et al., "Photoporphyrin IX Accumulation in Cells Treated with 5–Aminolevulinic Acid: Dependence on Cell Density, Cell Size and Cell Cycle," Int. J. Cancer 75:134–139 (1998).

Aizawa et al., "Method and medical Agent for Diagnosis of Arthritis" [on–line abstract database], Oct. 22, 1996, [retrieved on Oct. 2, 1998]. Retrieved from the internet: <URL: http://patents.uspto.gov/>.

Gierskcky et al., "Esters of 5–Aminolevulinic Acid as Photosensitizing Agents in Photochemotherapy" [on–line abstract database], Sep. 19, 1996, [retrieved on Oct. 2, 1998]. Retrieved from the internet: <URL:http://dips.patent-.gov.uk/>.

Jaffe, "Blood Lead Diagnostic Assay" [on–line abstract database], May 21, 1996, [retrieved on Oct. 2, 1998]. Retrieved from the internet: <URL: http://patents.uspto.gov/>.

Meserol, "Article of Manufacture for the Photodynamic Therapy of Dermal Lesion" [on–line abstract database], Apr. 9, 1996, [retrieved on Oct. 2, 1998]. Retrieved from the internet: <URL: http://patents.uspto.gov/>.

Meserol, "Method of Applying Photodynamic Therapy to Dermal Lesion" [on–line abstract database], Feb. 6, 1996, [retrieved on Oct. 2, 1998]. Retrieved from the internet: <URL: http://patents.uspto.gov/>.

Meserol, "Combination Controller and Patch for the Photodynamic Therapy of Dermal Lesion" [on–line abstract database], Dec. 12, 1995, [retrieved on Oct. 2, 1998]. Retrieved from the internet: <URL: http://patents.uspto.gov/>.

Zarate et al., "Illuminator and Methods for Photodynamic Therapy" [on–line abstract database], Aug. 15, 1995, [retrieved on Oct. 2, 1998]. Retrieved from the internet: <URL: http://patents.uspto.gov/>.

Aizawa et al., "Treatment of Arthritis using Derivatives of Porphorins" [on–line abstract database], Jul. 4, 1995, [retrieved on Oct. 2, 1998]. Retrieved from the internet: <URL: http://patents.uspto.gov/>.

Halling et al., "Method and Composition for Photodynamic Treatment and Detection of Tumors" [on–line abstract database], Apr. 18, 1995, [retrieved on Oct. 2, 1998]. Retrieved from the internet: <URL: http://patents.uspto.gov/>.

Trauner et al., "Photodynamic Therapy for the Destruction of the Synovium in the Treatment of Rheumatoid Arthritis and the Inflammatory Arthritides" [on–line abstract database], Nov. 29, 1994, [retrieved on Oct. 2, 1998]. Retrieved from the internet: <URL: http://patents.uspto.gov/>.

Aizawa et al., "Therapeutic Agent for Treating Atherosclerosis of Mammals", May 3, 1994, [retrieved on Oct. 2, 1998]. Retrieved from the internet: <URL: http://patents.uspto.gov/>.

Halling et al., "Method and Composition for Photodynamic Treatment and Detection of Tumors" [on–line abstract database], May 29, 1994, [retrieved on Oct. 2, 1998]. Retrieved from the internet: <URL: http://patents.uspto.gov/>.

Tanabe et al., "1.Alpha (or 24R), 25–Dihydroxy Vitamin D.sub.3 Derivatives" [on–line abstract database], May 26, 1992, [retrieved on Oct. 2, 1998]. Retrieved from the internet: <URL: http://patents.uspto.gov/>.

Hess et al., "Method for Treating Autoimmune Disease Using Succinylacetone" [on–line abstract database], May 19, 1992, [retrieved on Oct. 2, 1998]. Retrieved from the internet: <URL: http://patents.uspto.gov/>.

Hess et al., "Method of Preventing Graft Rejection in Solid Organ" [on–line abstract database], Apr. 14, 1992, [retrieved on Oct. 2, 1998]. Retrieved from the internet: <URL: http://patents.uspto.gov/>.

Aizawa et al., "Method for Detecting Cholesterol Deposited in Bodies of Mammals" [on–line abstract database], Mar. 5, 1991, [retrieved on Oct. 2, 1998]. Retrieved from the Internet: <URL: http://patents.uspto.gov/>.

Bommer et al., "Tetrapyrrole Polyaminomonocarboxylic Acid Therapeutic Agents" [on–line abstract database], Dec. 11, 1990, [retrieved on Oct. 2, 1998]. Retrieved from the internet: <URL: http://patents.uspto.gov/>.

Bard et al., "Novel DNA for Expression of Delta–aminolevulinic Acid Synthetase and Related Method" [on–line abstract database], Feb. 20, 1990, [retrieved on Oct. 2, 1998]. Retrieved from the internet: <URL: http://patents.uspto.gov/>.

Lai et al., "Storage–stable Porphin Compositions and a Method for Their Manufacture" [on–line abstract database], Nov. 21, 1989, [retrieved on Oct. 2, 1998]. Retrieved from the internet: <URL: http://patents.uspto.gov/>.

Marcker et al., "Post–transcriptional Heme Regulated Heterologous Gene Expression in Yeast Using the Leghemoglobin Leader Sequence" [on–line abstract database], Jul. 18, 1989, [retrieved on Oct. 2, 1998]. Retrieved from the internet: <URL: http://patents.uspto.gov/>.

Bommer et al., "Tetrapyrrole Therapeutic Agents" [on–line abstract database], Jun. 23, 1987, [retrieved on Oct. 2, 1998]. Retrieved from the internet: <URL: http://patents.uspto.gov/>.

Cidlowski et al., "Monoclonal Antibodies to Vitamin B–6 and Immunossay [sic]Method" [on–line abstract database], Jun. 24, 1986, [retrieved on Oct. 2, 1998]. Retrieved from the internet: <URL: http://patents.uspto.gov/>.

Cidlowski et al., "Monoclonal Antibodies to Vitamin B–6 and Immunoassay Method" [on–line abstract database], Aug. 14, 1984, [retrieved on Oct. 2, 1998]. Retrieved from the internet: <URL: http://patents.uspto.gov/>.

Fish et al., "Anticonvulsive Compositions and Method of Treating Convulsive Disorders" [on–line abstract database], Feb. 8, 1983, [retrieved on Oct. 2, 1998]. Retrieved from the internet: <URL: http://patents.uspto.gov/>.

Fish et al., "Anticonvulsive Compsitions and Method of Treating Convulsive Disorders" [on–line abstract database], Mar. 30, 1982, [retrieved on Oct. 2, 1998]. Retrieved from the internet: <URL: http://patents.uspto.gov/>.

Bey et al., "Novel Enzyme Inhibitors" [on–line abstract database], Jul. 7, 1982, [retrieved on Oct. 2, 1998]. Retrieved from the internet: <URL: http://patents.uspto.gov/>.

Nagasawa et al., "Process for Preparing a Therapeutic Agent" [on–line abstract database], Oct. 18, 1977, [retrieved on Oct. 2, 1998]. Retrieved from the internet: <URL: http://patents.uspto.gov/>.

Anderson & Parish, Optical Properties of Human Skin, New York, Plenum, p. 147 (1982).

Bommer, Hautuntersuchungen im gefilterten guarzlict. Klin Wochenschrift, 6:1142–1144 (1927).

Ghadially et al., "Mechanisms Involved in the Production of Red Fluorescence of human and experimental tumors" *J. Path. Bactiol.* 85:77–92 (1963).

Goff et al., "Effects of Photodynamic Therapy with Topical application of 5–aminolevulinic acid on normal skin of hairless guinea pigs", *J. of Photochem. & Photobiol. B:Biology* 15:239–51 (1992).

Gudin Dickson et al., "On the Role of Protoporphyrin IX Photoproducts in Photodynamic Therapy [news]", *J. of Photochem. & Photobiol. B:Biology* 29:91–3 (1995).

Konig et al., "In Vivo Autofluorescence Investigations on Animal Tumors", *Neoplasma* 36:135–8 (1989).

Lui et al., "In Vivo Fluorescence Spectroscopy Monitoring of BPD Verteporfin Concentration Changes in Skin tissue During Photodynamic Skin Cancer" *J. of Dermological Science* 12:87 (1996).

Lohman & Paul, "In Situ Detection of Melanomas by Fluorescence Measurement" *Naturwissenschaften* 75:201–2 (1988).

Sterenborg et al., "Evaluation of spectral Correction Techniques for Fluorescence Measurements on Pigmented Lesions In Vivo" *J. of Photochemistry and Photobiology B:Biology* 35:159–165 (1996).

Rhodes et al., "Iontophoretic Delivery of ala Provides a Quantitative Model for ala pharmacokinetics and ppix phototoxicity in human Skin" *J. of Investigative Dermatology* 108:87–91 (1997)

Barrett et al., "The Effect of Tissue and Cellular pH on the Selective Biodistribution of Porphyrin–type photochemotherapeutic Agents: a Volumetric Titration Study" *J. Photochem. & Photobiol. B:Biology* 6(3):309–23 (abstract) (1990).

Kochevar et al., "Photophysics, Photochemistry and Photobiology" in *Dermatology in General Medicine*, eds. Fitzpatrick et al., McGraw–Hill, vol. 1, p. 1627 (1993).

Martin et al., "Cutaneous Porphyrin Fluorescence as an Indicator of Antibiotic Absorption and Effectiveness", 12:758–764 (1973).

Kappas et al., "The Porphyrias", in *The Metabolic Basis of Inherited Disease I*, pp. 1302–1365, (1989).

Madsen et al., "Molecular Cloning, Occurrence, and Expression of a Novel partially Secreted Protein 'Psoriasin' that is Highly Up–regulated in Psoriatic Skin", *The Society of Investigative Dermatology*, 97(4):701–712 (1991).

Pudek et al., "Quantitative Fluorometric Screening Test for Fecal Porphyrins" *Clinical Chemistry* 37(6):826–831 (1991).

* cited by examiner

PHOTOACTIVATION OF ENDOGENOUS PORPHYRINS FOR TREATMENT OF PSORIASIS

TECHNICAL FIELD

The invention is in the field of diagnostic methods and light-activated treatments for skin disease, particularly the use of visible light for treatment of a diagnostically distinct form of psoriatic plaque exhibiting elevated endogenous porphyrin levels.

BACKGROUND ART

The emission of light at longer wavelengths after absorption of incident photons by chromophores is termed fluorescence. Under certain conditions, when human skin is illuminated with ultraviolet or visible light, cutaneous fluorescence can be detected. This phenomenon may be termed "autofluorescence" when it occurs in the absence of exogenously administered fluorescent compounds (Anderson, 1982; Zeng, 1993a).

Autofluorescence is believed to originate from various endogenous fluorophores, including nicotinamide adenine dinucleotide, elastin, collagen, flavins, amino acids and porphyrins. Porphyrins are naturally produced as intermediates in the biosynthetic pathway of heme. Protoporphyrin IX is the immediate precursor of heme. Spectrophotometry may be useful for distinguishing between porphyrins and other endogenous fluorophores based on the emission spectra of the fluorescent light.

Autofluorescence emission spectra and fluorescence images can be generated and recorded when incident light is shone on skin. An ultraviolet A emitting Wood's lamp may be used to assess cutaneous fluorescence for dermatologic diagnosis (Kochevar et al 1993). Macrospectrophotometry is a simple, flexible and efficient method of detecting cutaneous porphyrins illuminated with appropriate wavelengths of light; the technique is painless, takes only a few seconds and does not require a skin biopsy (Zeng et al., 1993).

Autofluorescence photographic images have been used to evaluate treatment responses in acne (Lucchina et al 1996, Martin R. J. et al 1973). Analysis and comparison of emission spectra has also been studied as a noninvasive diagnostic tool for skin diseases (Zeng et al 1995; Lohman 1988, Steremborg et al 1995).

Punctate red fluorescence on the nose and forehead under Wood's lamp illumination was reported as early as 1927 (Bommer, 1927), and has been linked to the presence in acne of porphyrins generated by Propionibacterium acnes (Cornelius, 1967; McGinley, 1980; Lee et al 1978; Konig et al, 1992; Johnson, 1987; Lucchina, 1996). The presence of red skin autofluorescence at the centre of experimentally produced or grafted tumours has been reported for rats (Policard, 1924; Gougerot, 1939; Rochese, 1954), mice (Konig, 1989), rabbits (Ghadially, 1960) and for chemically-induced squamous cell carcinoma in the cheek pouch of the hamster (Harris, 1987). In the latter case, the tumours were examined microscopically and the red fluorescence was shown to be restricted to the surface keratin layer (Harris, 1987). Similar red autofluorescence has also been reported for human oral and oropharyngeal squamous cell carcinoma (Harris, 1987; Dhingra, 1996; Konig, 1994), dysplastic areas of the oral mucosa (Ingrams et al., 1997) as well as normal human tongue (Harris et al, 1987).

In studies where spectroscopic analysis was performed, the fluorescence emission peak was centred around 636–640 nm (Konig et al., 1994; Dhingra, 1996). Konig et al. (1994) believed it was related to bacterial synthesis of porphyrins whereas Dhingra et al (Dhingra, 1996) hypothesized that the red autofluorescence could be caused by a build-up of endogenous porphyrins by tumor cells.

Macrospectrophotometry may be used to detect skin porphyrin in patients receiving exogenous porphyrins, or porphyrin precursors, for photodynamic therapy, and to follow the time course accumulation of porphyrins in photodynamic therapy (Lui, 1996; Rhodes, 1997; Stringer, 1996). The intensity of the fluorescence emission peaks has been shown to correlate with the amount of exogenous porphyrin precursor applied on the skin (Rhodes, 1997).

Porphyrins that absorb light may induce photochemical reactions that can be toxic to living cells. Such toxicity may be due to the local generation of reactive oxygen species (Arakane et al., 1996). The toxicity generated by light activation of pharmacologically elevated levels of porphyrins is the basis for photodynamic therapy which may be used to treat a variety of conditions, including cancer (see U.S. Pat. Nos. 5,211,938; 5,234,940; 5,079,262; all to Kennedy et al.) The low levels of natural porphyrins present in most tissues are not known to cause deleterious photochemical effects (Goerz et al., 1995).

Very low levels of porphyrins have been shown to be present in biopsies of human skin containing the epidermis and dermis (Goerz et al., 1995; Pathak 1963), as well as whole epidermis isolated by suction blister (Gog, 1973). Protoporphyrin IX was the predominant porphyrin type (Goerz et al., 1995; Gog, 1973) except in porphyria cutanea tarda patients, where uroporphyrin was predominant (Malina, 1978). Goerz et al., 1995, report that skin does not normally contain sufficient levels of porphyrins to allow one to perform photodynamic therapy, and consequently photodynamic therapy requires exogenous addition of photosensitizer.

Psoriasis is a hyperproliferative and inflammatory disease characterized by red scaly plaques on the skin. Current accepted or experimental methods of using light to treat psoriasis involve either the use of potentially carcinogenic ultraviolet light alone or the administration of exogenous photosensitizer, or a precursor of a photosensitizer (such as aminolevulinic acid), followed by light exposure. Blue and red light can activate protoporphyrin IX and this has been used to improve psoriasis when exogenous aminolevulinic acid (ALA) is applied on the skin to induce protoporphyrin IX synthesis (Boehncke, 1994; Nelson, 1995). However, photosensitizers or photosensitizer precursors such as ALA may have adverse side effects when administered topically or systemically. For example, they may induce photosensitivity on clinically normal skin.

SUMMARY OF THE INVENTION

In one aspect, the invention provides a diagnostic method for identifying psoriatic plaques having elevated porphyrin levels, comprising assaying psoriatic plaques for autofluorescent light. Autofluorescent light may be visualized under ultraviolet or visible light illumination. For example, red autofluorescence in some psoriatic plaques may be directly visualized under ultraviolet light using a Wood's lamp. The autofluroescence of psoriatic plaques may also be analysed using spectrophotometry, such as laser-induced macrospectrophotometry or micro-spectrophotometry, to detect the fluorescent emissions of a porphyrin, such as an emission peak around 630–635 nm that may be indicative of protoporphyrin IX.

Throughout this specification, any reference to "endogenous" porphyrin with reference to a psoriatic plaque refers to porphyrins which are present in a psoriatic plaque not as a result of the application of exogenous porphyrins (such as Photofrin®BPD-MA or others) or their precursors (such as ALA). Thus, endogenous porphyrins referred to herein arise within the plaque and do not include porphyrins present in the plaque as a result of application of a porphyrin to the patient or which could arise within a plaque as a result of administration of a porphyrin precursor to the patient. Endogenous porphyrin levels are 'elevated' when they are higher than in normal skin, particularly when such levels are detectable as red autofluorecence.

In another aspect of the present invention, psoriatic plaques with elevated endogenous porphyrin levels may be treated with visible light. The spectrum of the visible light used may be optimized to match the absorption spectrum of a porphyrin detected in the plaque. For example, blue light may be used to treat plaques with elevated levels of protoporphyrin IX.

Optionally, endogenous porphyrin levels in a psoriatic plaque may be elevated by administering a topical composition to the psoriatic plaque to modify some of its characteristics including, but not restricted to: the pH, iron levels, the degree of hydration (eg. with occlusion), temperature, calcium ion concentration, local estrogen level, electrical conductivity, and/or the oxygenation in the plaque. These characteristics may be modified alone or in combination. For example, a topical composition may be applied that buffers the pH of at least a portion of the psoriatic plaque between about pH 5 to 8, or pH 6 to 7.5, or pH 5.7 to 6.5, or about pH 6 or about pH 6.1 or about pH 7.4.

Iron chelators may be used in alternative embodiments of the invention when applied topically to enhance endogenous porphyrin levels, particularly protoporphyrin IX levels. In various embodiments, appropriate iron chelators may be 1, 2-diethyl-3-hydroxypyridin-4-one (CP94) desferrioxamine (DEF), or ethylenediaminetetraacetic acid (EDTA).

Psoriatic plaques treated as described above to elevate endogenous porphyrin levels in the plaque may be treated with visible light. For example, blue light, or light having a wavelength between about 400 and 500 nm, may be used to treat plaques exhibiting red autofluorescence, or plaques in which protoporphyrin IX levels are elevated to levels that are detectable by autofluorescence. The visible light may be monochromatic, such as laser light, or polychromatic. Polychromatic light may be filtered to remove unwanted wavelengths, such as ultraviolet light having a wavelength less than 400 nm. Visible light may be used for treatment, having a wavelength generally between 390 and 770 nm.

DETAILED DESCRIPTION OF THE INVENTION

In accordance with one aspect of the present invention, it is disclosed that elevated levels of endogenous porphyrins are present in some psoriatic plaques as compared to normal skin and other skin diseases. The porphyrin levels are sufficiently high to enable visualization of pink-red fluorescence on psoriatic plaques with Wood's lamp. Any method which allows for excitation of and detection of fluorescent emission, including macrospectrophotometry and microspectrophotometry, may be used to detect the presence of endogenous porphyrins in psoriatic plaques.

Elevated levels of endogenous porphyrins may be detected by red fluorescence when skin is illuminated with light having appropriate wavelengths, especially about 400–410 nm. Such autofluorescence is preferably visible to the naked eye. In accordance with one embodiment of the present invention, elevated endogenous porphyrin levels are levels of porphyrins that are detectable as visible red autofluorescence following excitatory illumination. Excitatory illumination may be with polychromatic light, in one aspect comprising light of wavelengths between about 400 and 500 nm, or between 400 and 450 nm. In one embodiment, UVA (generally 320–400 nm) or blue (generally 400–455 nm) light may be used for excitatory illumination. Laser light having a wavelength of about 442 nm may be used for excitatory illumination.

Figure 1:
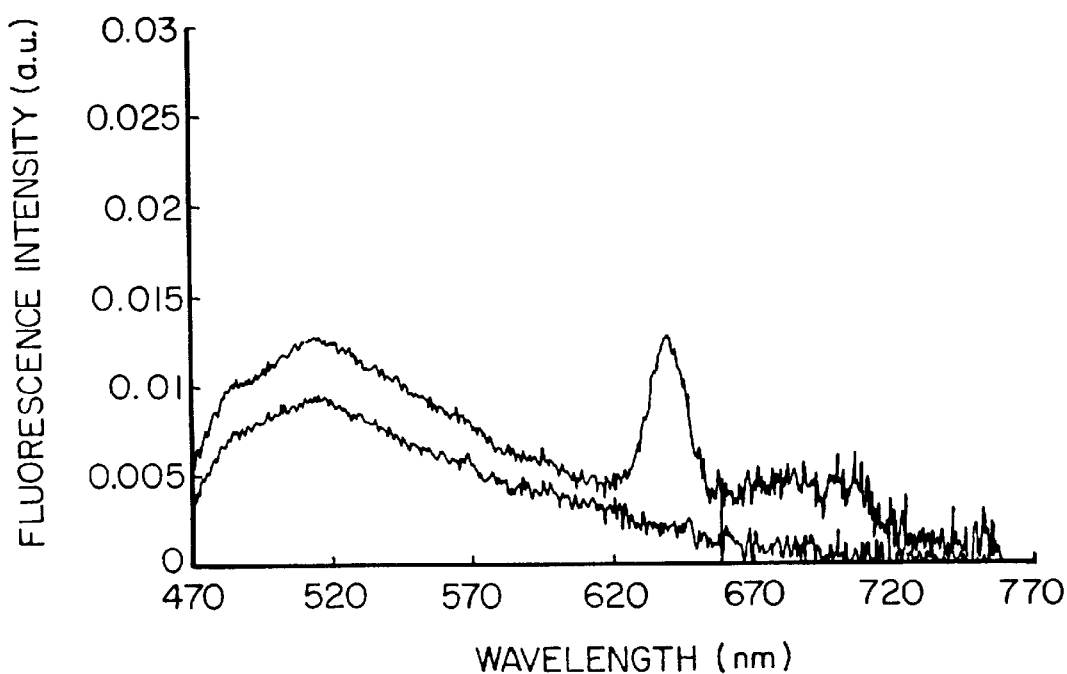
FIG. 1: Macrospectrophotometric emission spectra of normal skin (lower line) and psoriatic skin (upper line) from the same patient. A peak at approximately 635 nm is present only for psoriatic skin.

FIG. 1 shows that Macrospectrophotometric emission spectra from normal skin of psoriatic patients are similar to those described for normal human skin in previous studies (Zeng et al., 1993a). FIG. 1 shows that psoriatic plaques, however, reveal a unique emission peak at about 635 nm. This wavelength corresponds to the in vivo emission peak generated by protoporphyrin IX when the exogenous precursor ALA is applied to the skin (Goff 1992, Stringer 1996, Rhodes 1997). Evidence of a photoproduct (which may be produced as a result of the photochemical breakdown of porphyrin) may be observed in an absorbtion peak at about 670 nm (this corresponds to the wavelength of the major excitable photoproduct of protoporphyrin IX reported by Gudgin Dickson et al., 1995).

Macrospectrophotometric analysis reveals that the 635 nm peak is present on psoriatic plaques and absent from normal skin and from all other skin diseases studied. The use of a 405–410 nm light to induce autofluorescence could increase the sensitivity of macro-spectrophotometric analysis by making use of a broad porphyrin excitation band centred around 407 nm.

As set out in Example 1, a 635 nm macrospectrophotometric emission peak was present in the plaques of 32 of the 70 (46%) patients with psoriasis studied, where emission spectra were recorded only for one or two plaques for most patients. The 635 nm peak may be absent from one plague but present on another in the same patient. Looking at all of a patient's plaques with a Wood's lamp for visible pink-red fluorescence and recording the emission spectrum from the most fluorescent plaque may be a more efficient method to identify a higher percentage of patients showing the 635 nm peak. Some patients fail to show a 635 nm peak in any plaques. The frequency of occurrence of the 635 nm peak may vary between chronic plaque type psoriasis, erythrodermic psoriasis and pustular psoriasis.

Macrospectrophotometry can detect and quantify porphyrins in the skin but provides no information on their histological location. The ability of the microspectrophotometer to obtain emission spectra on micro-locations on a tissue section may be exploited for misroscopic porphyrin localization (Zeng et al., 1993b).

In Example 1, the emission spectra observed from all levels of normal skin for psoriatic patients are similar to spectra obtained in previous studies from normal skin (Zeng et al., 1993a). Systematic recording and analysis of spectra from different levels of psoriatic skin sections reveals that the 635 nm fluorescence signal originated specifically from the stratum corneum.

Analysis of acid extracts from psoriatic scales may be used to confirm the presence of porphyrins in plaques and identify the specific porphyrin species involved. In Example 1, fluorometric analysis reveals the typical spectral pattern of porphyrins in acidic solution, with a single excitation peak at 407 nm and two emission peaks at 602 and 658 nm (Kappas et al., 1989). This pattern was absent in scales of all 3 controls studied, suggesting either that they did not contain porphyrins or that the porphyrin concentration was too low to be detected by this technique. Although excitation and emission spectra of pure protoporphyrin IX in HCl were very similar to spectra from psoriatic scale extracts in Example 1, precise porphyrin identification may not be possible with fluorometry alone, as excitation and emission peaks of the different porphyrins are very close to each other.

Separation of porphyrins with high performance liquid chromatography (HPLC) may be undertaken to identify the type of porphyrin present in the psoriatic plaques. In Example 1, one porphyrin peak was present in all 5 patients studied and its retention time was similar to that of protoporphyrin IX, indicating that protoporphyrin IX is the predominant typed of porphyrin present. Other porphyrins may be present, but at concentrations that are too low to be detected by HPLC techniques.

As disclosed in Example 2, endogenous porphyrins in psoriatic plaques may be activated with visible light to treat psoriatic plaques having elevated porphyrin levels. In accordance with this aspect of the invention, visible light may be used to treat psoriasis in patients having psoriatic plaques with elevated levels of endogenous porphyrins. Such patients may be identified using Wood's light examination, autofluorescence visual aid devices, macrospectrophotometry, microspectrophotometry or a combination of such methods or equivalents thereof. Treatment conditions may be optimized by physicians in accordance with particular clinical findings. For example, patients presenting with elevated levels of protoporphyrin IX in their psoriatic plaques may be treated with visible light administered to the psoriatic plaques.

Skin conditions may be optimized to increase the endogenous synthesis of porphyrins in psoriatic plaques. A topical formulation may be applied to psoriatic plaques to optimize skin conditions such as pH, iron levels, degree of hydration (eg. occlusion), temperature, calcium concentration, electrical conductivity, local estrogen concentration, and oxygenation for increased production or accumulation of endogenous porphyrins. In some patients, an optimum pH for protoporphyrin IX production may be pH 6.1. It may be preferable to lower iron levels or to increase estrogen levels in the plaque. The concentration of endogenous porphyrins may be monitored using Wood's light examination, autofluorescence visual aid devices, macro-spectrophotometry, microspectrophotometry or combinations thereof.

EXAMPLE 1

A total of 70 patients with psoriasis (Table I) and 100 patients with a variety of other dermatological diseases were investigated (Table II).

Macrospectrophotometry was performed on all patient to assess the presence of red autofluorescence and skin biopsies were taken from 6 patients with psoriasis for detailed microscopical and biochemical analysis.

Autofluorescence spectra of psoriatic and surrounding normal appearing skin were recorded (101 spectra in 70 patients) using a computerized fluorescence spectroanalyzer system (Zeng, 1995). The light source for fluorescence excitation was a 442 nm He-Cd laser hooked up to a spectrometer (Ocean Optics Inc., Dunedin, Fla., USA, PC 1000) and a personal computer. The laser light reached the skin through six optical fibers. The emitted fluorescent light was collected with another optical fibre and transmitted to the spectrometer for spectral analysis.

TABLE I

Location and type of psoriasis studied

| Type | Location | Number of Lesions Studied* |
|---|---|---|
| Vulgaris | Face | 3 |
|  | Limbs | 58 |
|  | Trunk | 23 |
|  | Buttocks | 2 |
|  | Not recorded | 2 |
| Palmo-plantar | Palm | 6 |
|  | Sole | 1 |
| Nail | Nail | 4 |
| Scalp | Scalp | 2 |

*A total of 101 lesions in 70 patients were assessed for red fluorescence using macrospectrophotometry

TABLE II

Clinical diagnosis of patients studied

| Diagnosis | Number of Patients |
| --- | --- |
| Psoriasis | 70 |
| Contact dermatitis | 11 |
| Atopic dermatitis | 3 |
| Seborrheic dermatitis | 2 |
| Acne | 10 |
| Wart | 12 |
| Actinic keratosis | 18 |
| Port wine stain | 3 |
| Porokeratosis | 3 |
| Discoid lupus erythematosus | 2 |
| Rosacea | 3 |
| Sebaceous hyperplasia | 4 |
| Other | 29 |

Three millimeter punch biopsies of psoriatic plaques and normal skin were performed on 6 psoriatic patients demonstrating a macrospectrophotometric emission peak above 600 nm. For the first 3 patients, the biopsy specimens were frozen in liquid nitrogen-cooled isopentane and sections were cut perpendicular to the plane of the epidermis at a thickness of 20 $\mu$m. The sections were placed unfixed on glass slides for microspectrophotometric analysis. One section from each specimen was fixed in acetone for 10 minutes and stained with hematoxylin and eosin. Care was taken to minimize exposure of the tissue to ambient light. The biopsies from the last 3 patients were incubated in the dark at 4C. in Hank's buffered saline solution containing 0.25% trypsin (Madsen, 1991). After overnight incubation the epidermis was mechanically separated from the dermis, placed on glass slides, and frozen at −80° C. until analyzed by microspectrophotometry. The dermis was frozen in liquid nitrogen-cooled isopentane, from which 20 $\mu$m thick frozen sections were cut. Stratum corneum and/or psoriatic scales for microspectrophotometric analysis were obtained by tape stripping using standard Scotch tape (3M® Canada Inc., London, Ontario) applied to the normal or psoriatic skin of 3 patients for 5 seconds. This procedure was repeated 3 times with the same piece of tape which was subsequently attached to a glass slide for analysis.

The skin biopsies, isolated epidermis, and tape-stripped stratum corneum were analyzed using a microspectrophotometer (Zeng, 1993). A 442 He-Cd laser was connected to an inverted Nikon microscope with a 400 $\mu$m optional fibre equipped with a microlens. A 480 nm long pass filter was placed after the objective. Another optical fibre was used to collect light from a specific microlocation on the slide and transmit the collected light to an optical multichannel analyzer for a spectral analysis. Calibration of the device was performed with a mercury lamp. This set up enabled the recording of the autofluorescence emission spectrum from selected microlocations as small as 24 nm. At least 2 spectra were recorded from the stratum corneum, mid epidermis, lower epidermis and dermis of normal and psoriatic skin for each of the 3 patients. At least 2 spectra were also recorded from the isolated epidermis and the corresponding frozen sections of the dermis, for psoriatic and normal skin. The thickness of all frozen sections used for the microspectrophotometric analysis was 20 microns. For tape stripped stratum corneum, the emission spectrum of the scales attracted between the microscopic slide and the tape was also recorded for 3 patients. The emission spectrum of tape alone without scales was recorded as a control. Microspectrophotometry was carried out on vertical tissue sections (i.e. sections cut perpendicular to the skin surface) for analysis of intact whole skin and isolated dermis, whereas isolated epidermis and scales collected by tape stripping were analyzed in a horizontal orientation as sheets of cells.

Scales were collected with a dermatological curette from plaques of 8 patients with psoriasis exhibiting a 635 nm emission peak on macrospectrophotometry. To serve as controls, scales were also collected from 2 patients with atopic dermatitis and 1 patient with an exfoliative drug eruption. Scales were added to 3M HCl and incubated with constant shaking at room temperature for 30 minutes. The mixtures were then centrifuged at 3000 RPM for 10 minutes and the supernatants collected (Pudek, 1991). A LS-5 Perkin-Elmer fluorometer was used to obtain excitation and emission spectra of these acid extracts for 5 patients with psoriasis and the 3 controls. To generate excitation spectra, the acid extracts were scanned from 350 to 440 nm with emission monitored at 601 nm as this wavelength corresponds to an emission peak for porphyrins in acidic solution. For fluorescence emission spectra, a fixed excitation of 403 nm was used and the emission was recorded from 550 to 700 nm. A Hewlett-Packard high performance liquid chromatograph was used to separate and identify the porphyrins for 5 patients with psoriasis. The supernatants extracts were filtered and injected onto a C18 reversed phase column. The porphyrins were eluted with a linear gradient of 10% solvent A (10/90 (by volume) mixture of acetonitrile and 1 mol/L ammonium acetate buffer at pH 5.16) to 90% Solvent B (10/90 (by volume) mixture of acetonitrile/methanol). The flow rate was 1.5 ml/min. To detect porphyrins the excitation was set at 401 nm and the emission above 580 nm was recorded. Porphyrin standards (Porphyrin products, Logan Utah, USA) diluted in 3M HCl were also eluted using the same parameters.

For clinical fluorescence photography, a Nikon F-601 camera with a 60 mm micro AF lens set at f2.8 was used. Psoriasis plaques were illuminated in the dark with a Wood's lamp (UVP, Upland Calif., USA, Model B 100 AP) and photographs were taken using a 1600 ASA Fujichrome film with exposure times ranging from $\frac{1}{30}$ sec to $\frac{1}{4}$ sec.

Figure 5:
FIG. 5: Fluorescence with Wood's lamp seen on the back of a patient with extensive psoriasis. Fluorescence is emitted from most of the area of each plaque and is pink-red, standing out from the background illumination on the patient's skin.
Figure 6:
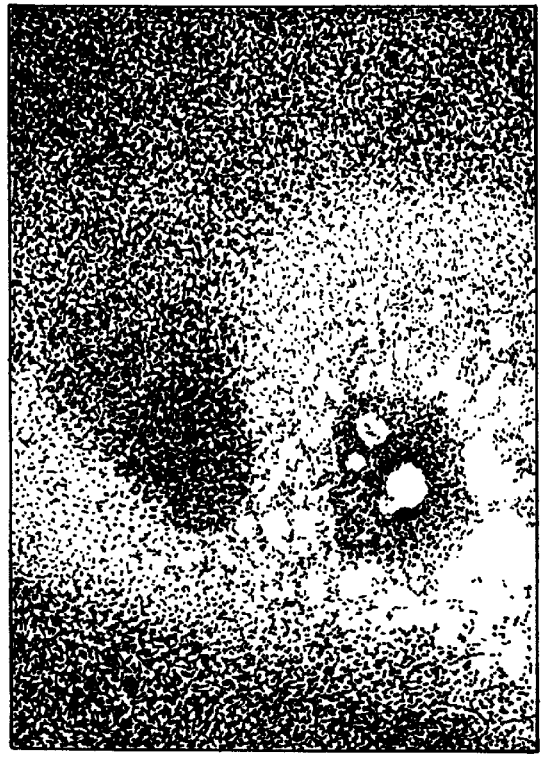
FIG. 6: Heterogeneous fluorescence of a psoriatic plaque on a patient's knee illuminated with Wood's lamp (upper portion). As with FIG. 5, the fluorescence is a pink-red but in this case is emitted from portions of the plaque. A non-fluorescent psoriatic plaque is also seen (lower portion of FIG. 6) as a dark area.
Figure 7A:
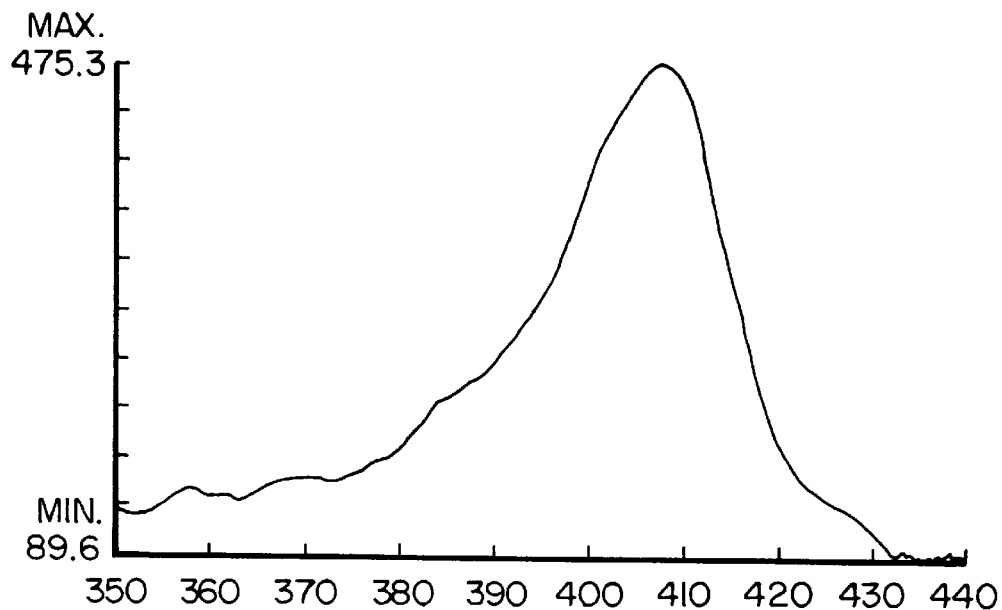
FIG. 7: Excitation (A) and emission (B) spectra of acid extracts from psoriatic scales are similar to excitation (C) and emission (D) spectra of protoporphyrin IX in HCl.
Figure 7B:
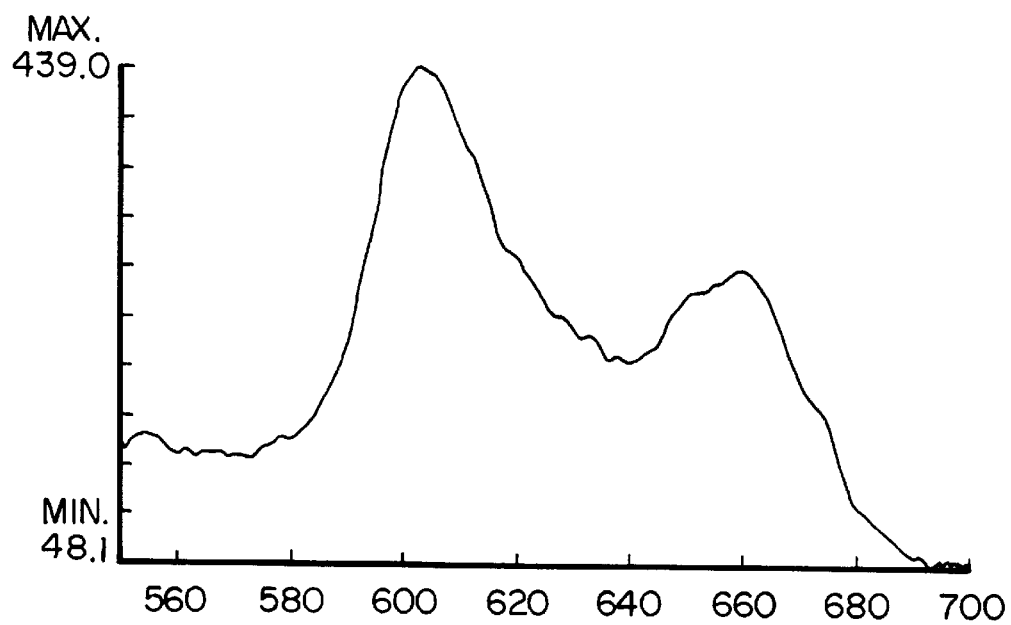
Figure 7C:
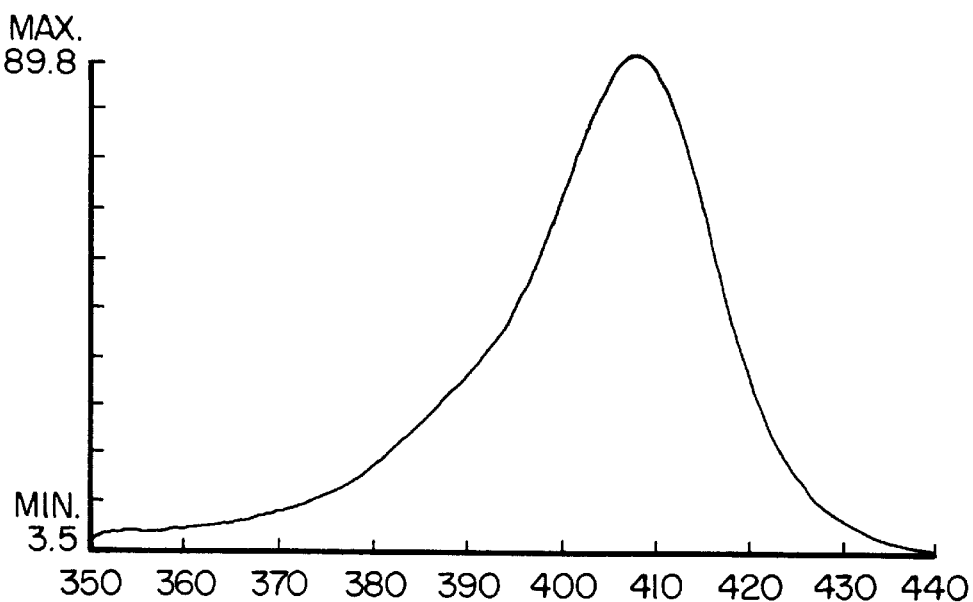
Figure 7D:
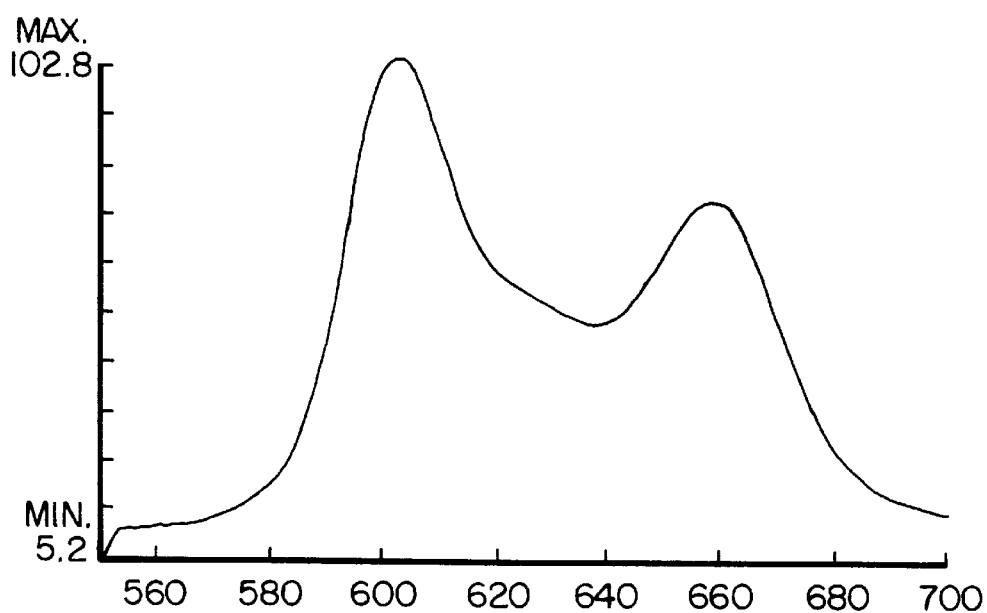

Bright pink-red fluorescence was seen on psoriatic skin illuminated with Wood's lamp (FIG. 5). The fluorescence could be heterogeneous within a plaque as shown in the upper portion of FIG. 6. Areas with more scales were found to display brighter fluorescence within a given plaque. In the same patient, certain plaques did not exhibit the pink-red fluorescence (upper plaque of FIG. 6). Pink red fluorescence was never seen on normal skin of psoriatic patients. When superficial scales from a psoriatic plaque were gently removed and placed either on the patient's normal skin or on the normal skin of someone without psoriasis, pink-red fluorescence was seen (data not shown).

The fluorescence emission spectrum from normal skin of patients with psoriasis showed an increase in fluorescence intensity from 470 nm to about 520 nm followed by a monotonic decrease from 520 nm to the beginning of the infrared (FIG. 1). The fluorescence emission spectrum of psoriatic skin exhibited a unique peak around 635 nm (FIG. 1) which was absent on all spectra from normal appearing skin obtained from psoriatic patients. Based on visual examination, the remainder of the fluorescence emission spectra of psoriatic skin were not significantly different from those obtained with normal skin. Of 70 psoriatic patients studied, 32 (46%) presented an emission peak around 635 nm when macrospectrophotometry was performed on a psoriatic plaque. The mean wavelength of the peak was 634.9± 0.9 (±SD) from 11 spectra from 9 patients. The 635 nm peak was absent from all 100 emission spectra obtained under the same conditions from patients with other skin diseases. Another peak around 670 nm was present if laser light was shone on the skin for more than 10–15 seconds before recording the spectra (data not shown). This peak was never present on normal skin of psoriatic patients.

Figure 2A:
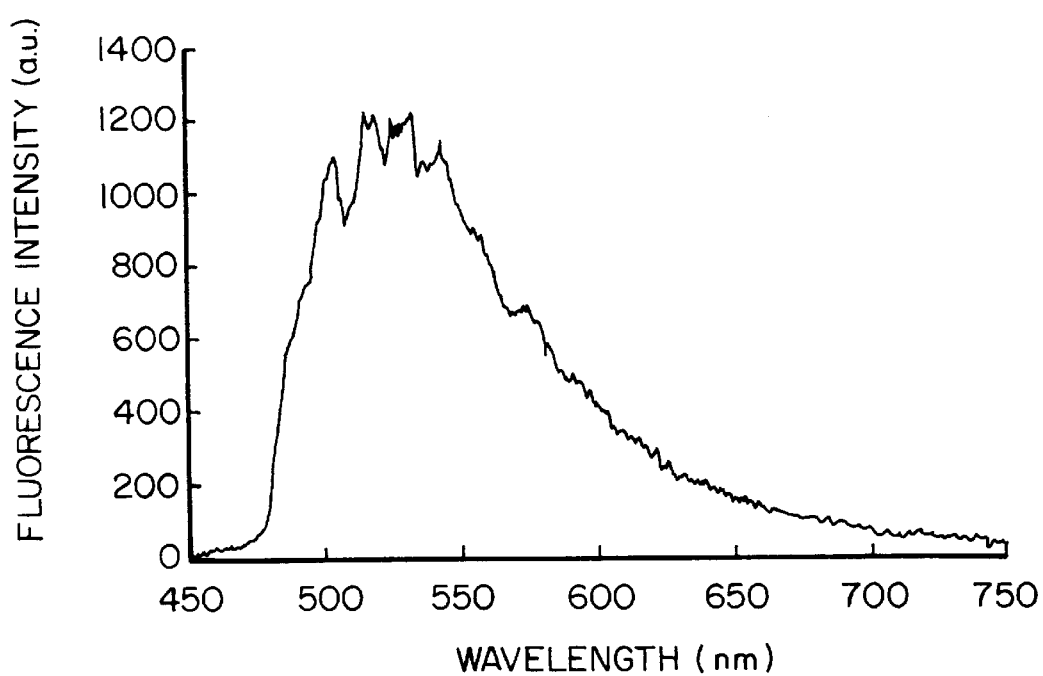
FIG. 2: Microspectrophotometric emission spectra of isolated epidermis from normal (A) and psoriatic (B) skin with the corresponding normal (C) and psoriatic dermis (D). A peak around 635 nm is present only in psoriatic epidermis (B).
Figure 2B:
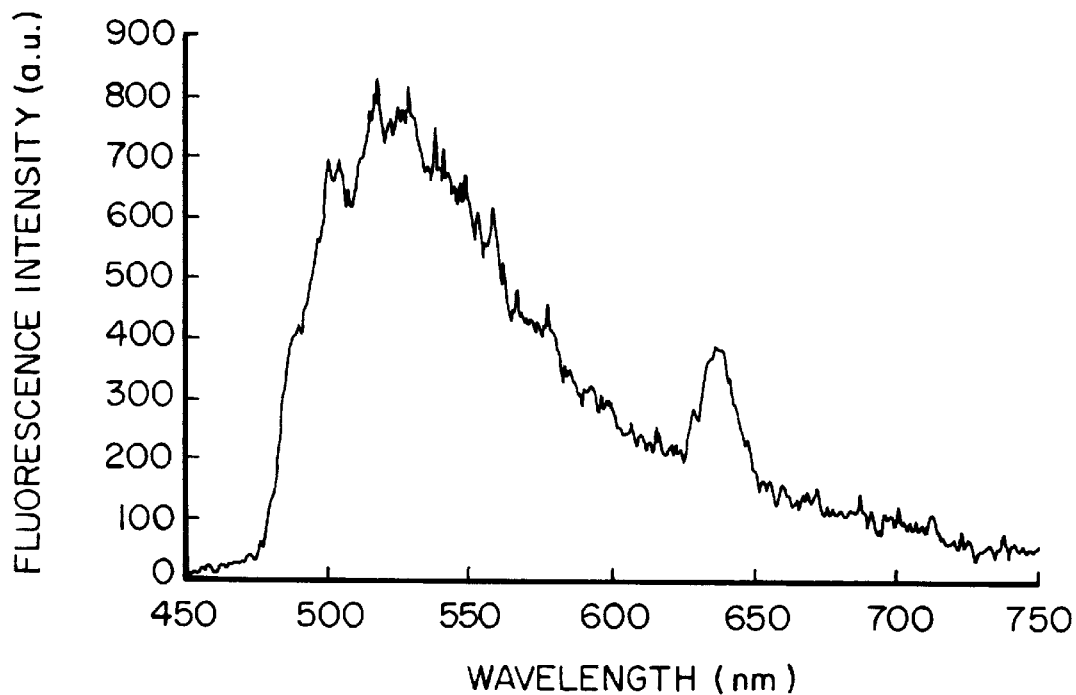
Figure 2C:
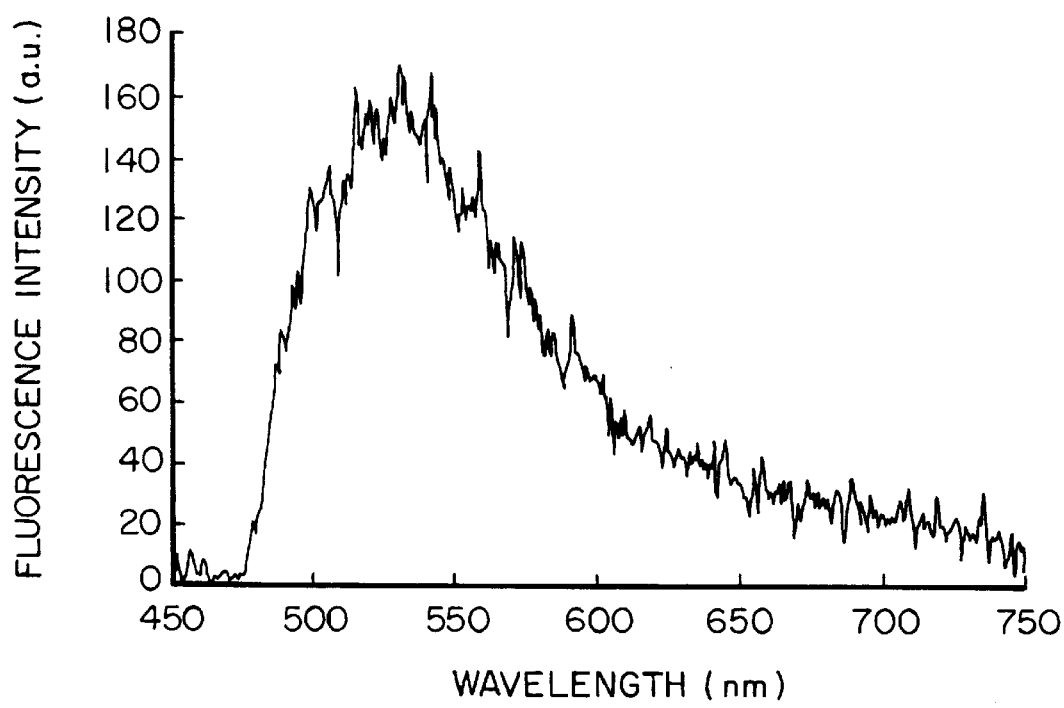
Figure 2D:
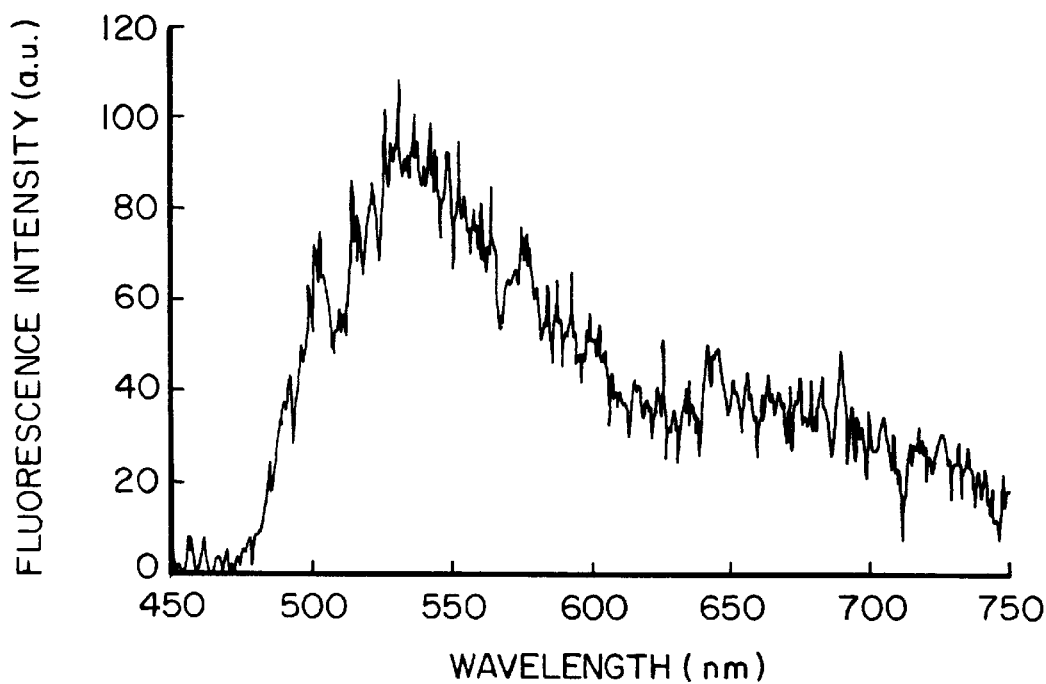
Figure 3A:
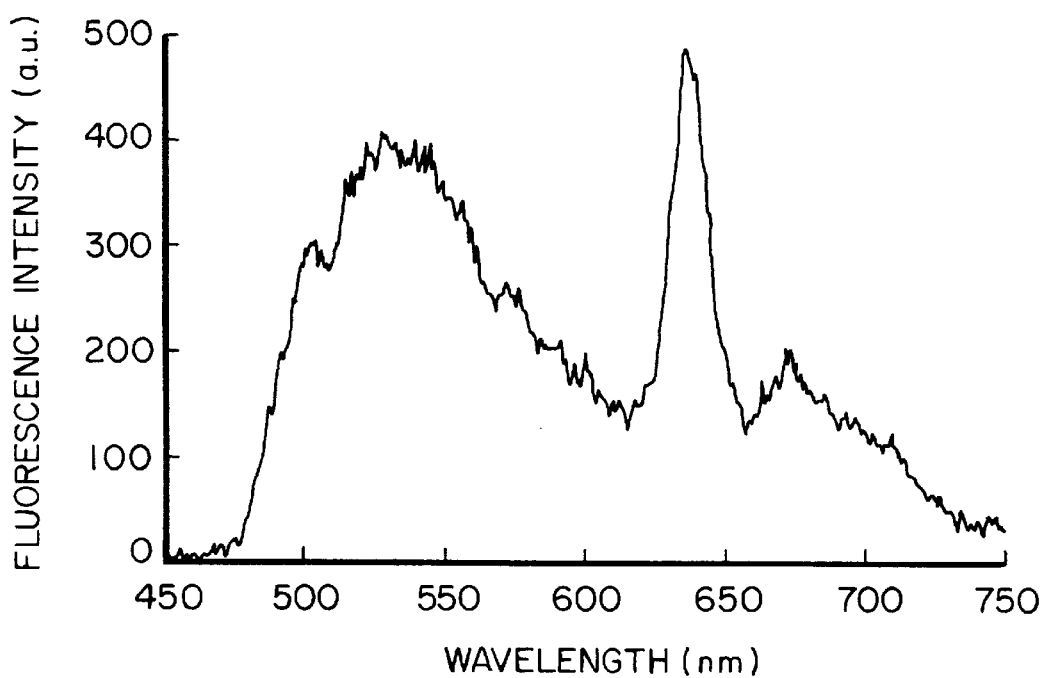
FIG. 3: Microspectrophotometric emission spectra of psoriatic stratum corneum (A), normal skin stratum corneum (B), psoriatic mid epidermis (C), and psoriatic dermis (D). Only the psoriatic stratum corneum shows a peak around 635 nm (A).
Figure 3B:
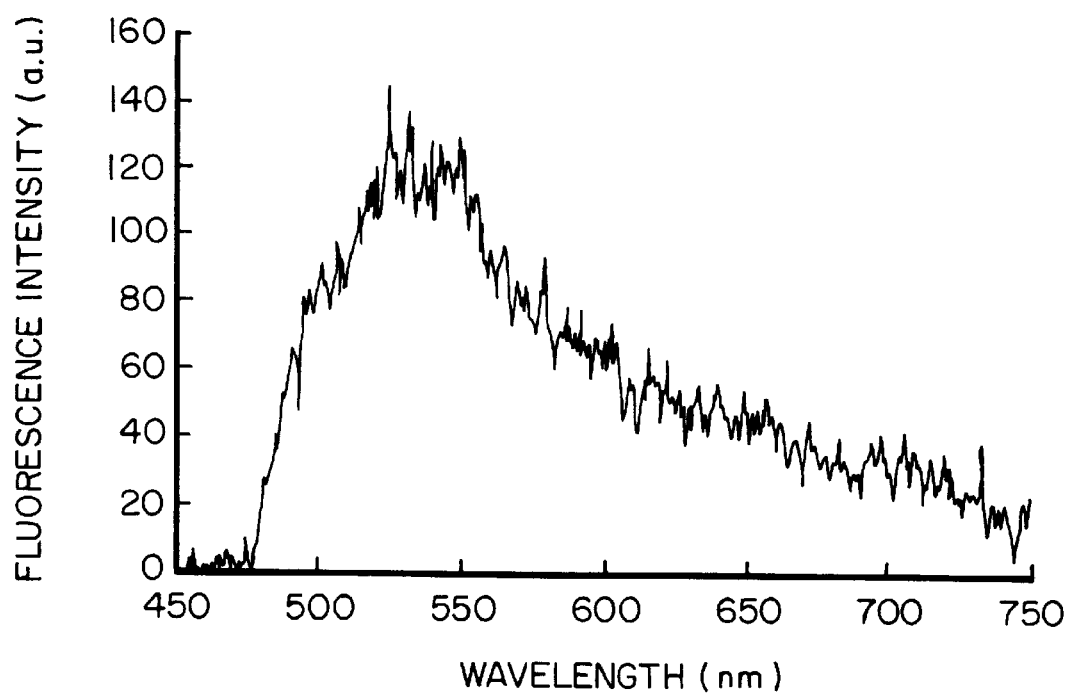
Figure 3C:
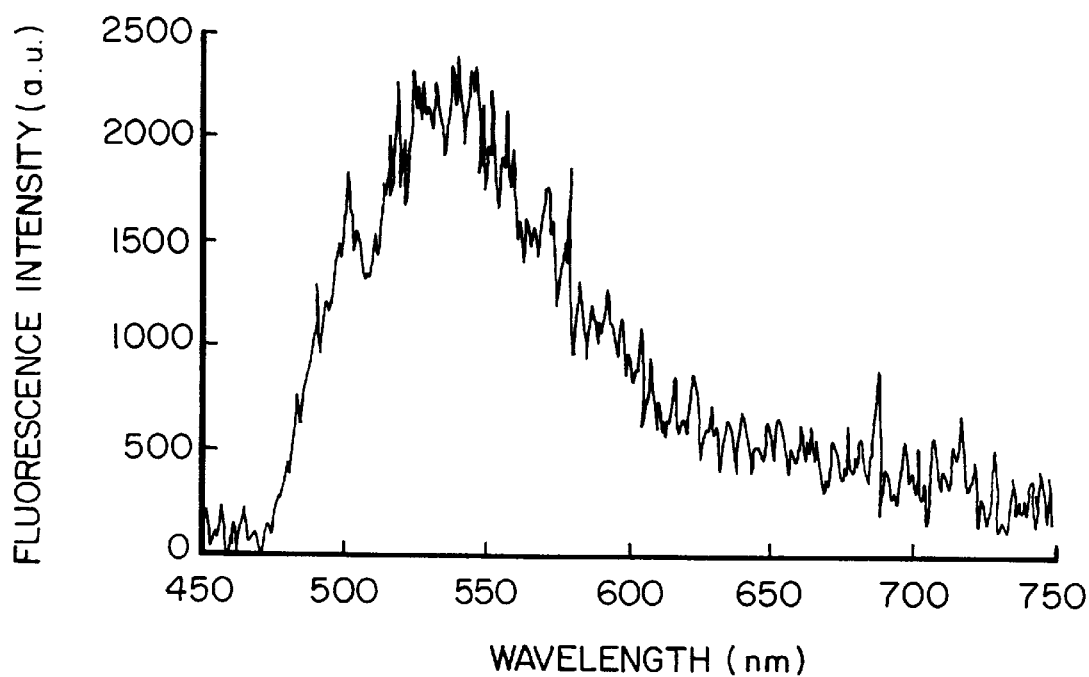
Figure 3D:
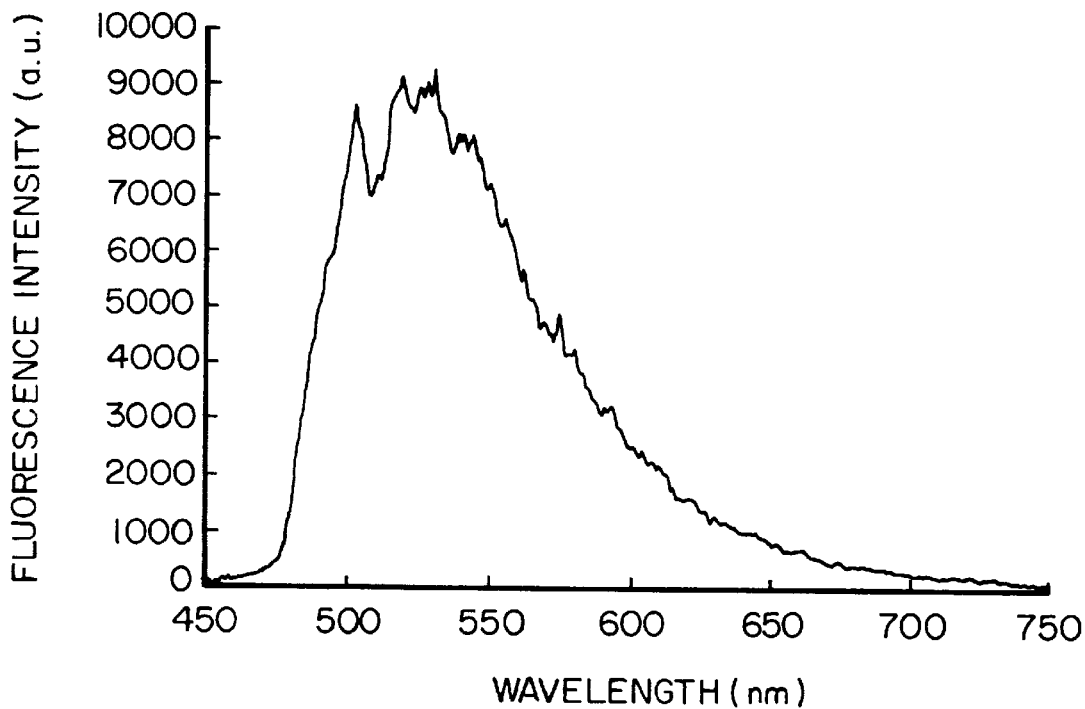

The microscopic emission spectrum of isolated epidermal sheets from normal-appearing skin of patients with psoriasis showed a sharp increase in autofluorescence around 475nm followed by a maximum around 525 nm and a gradual decrease towards the infrared (FIG. 2a). In contrast, the emission spectrum of isolated psoriatic epidermis sheets demonstrated a peak around 635 nm in all 3 patients studied (FIG. 2b). The 635 nm peak was absent from the corresponding dermis of psoriatic biopsies and no major differences were visually observed between the dermal emission spectra of normal and psoriatic skin (FIG. 2c,d). Microspectrophotometry was subsequently performed on vertical sections of whole skin biopsies to localize the epidermal component responsible for the 635 nm peak. FIG. 3a shows that an intense peak is present around 635 nm on the emission spectrum of the stratum corneum in psoriatic skin. This peak was absent in other layers of psoriatic epidermis, psoriatic dermis and normal skin stratum corneum (FIG. 3b–d). The wavelength of the emission peak was 637.4± 1.5 (±SD) for 38 spectra from 6 patients. A smaller peak around 670 nm was present on the emission spectrum of psoriatic stratum corneum (FIG. 3a). The intensity of this peak gradually increased with a corresponding decrease in the intensity of the 635 nm peak when the laser light was shone at the same location and repeated spectra were recorded (data not shown).

Figure 4:
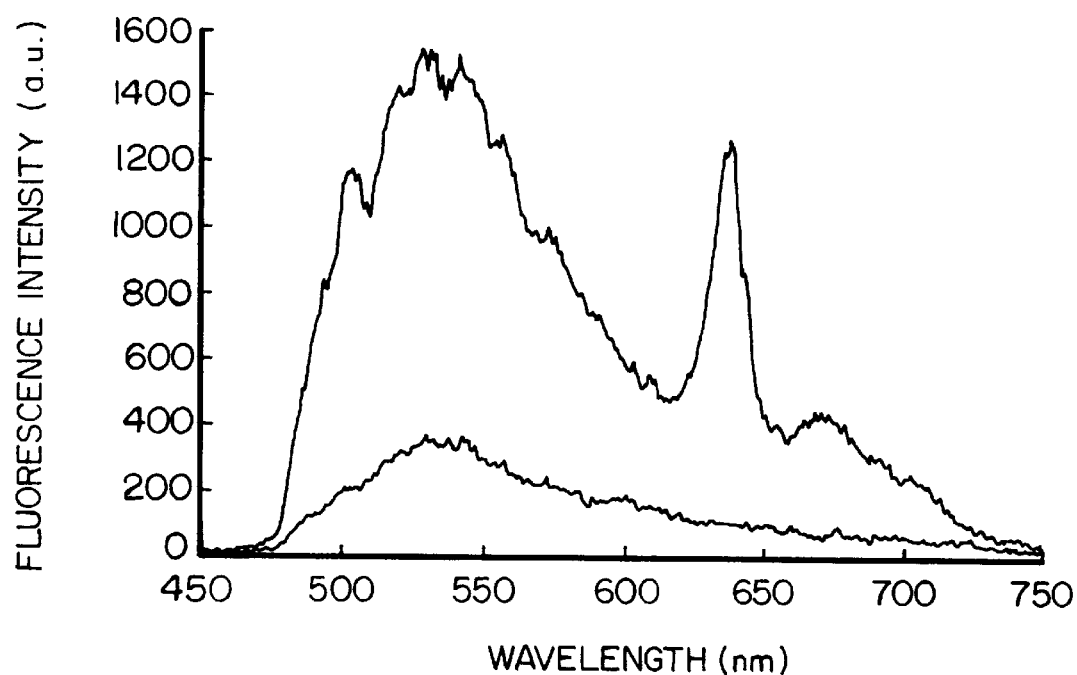
FIG. 4: Microspectrophotometric emission spectrum of tape stripped scales showing a peak around 635 nm (upper line) with tape alone (lower line) serving as a negative control.

Microscopic spectrophotometry was performed on tape stripped scales from psoriatic plaques to confirm the stratum corneum origin of the peak. A distinct peak about 635 nm is present on tape with scales and absent on tape without scales (FIG. 4).

Acid extracts from scales of psoriatic plaques were first analyzed with a fluorometer. The excitation spectra showed a single peak with a maximum of 407 nm whereas two peaks were present around 602nm and 660 nm of the emission spectra (FIG. 7). The spectra of pure protoporphyrin IX in HCl were similar with a single excitation peak at 407 nm and two emission peaks at 602 nm and 658 nm (FIG. 7). All 5 acid extracts of psoriatic scales showed a similar pattern. No peaks were observed on the excitation and emission spectra of acid extracts from scales of 2 patients with atopic dermatitis and 1 with exfoliative drug eruption (not shown).

Figure 8A:
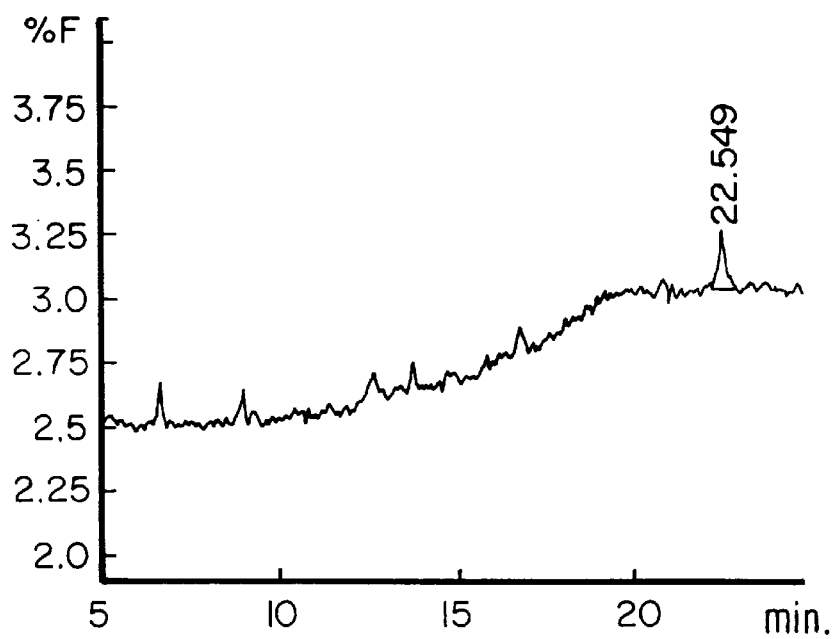
FIG. 8: HPLC elution profiles of acid extracts from psoriatic scales (A) and porphyrin standards (B). The predominant peak at 22.5 min. matches the retention time of protoporphyrin IX.
Figure 8B:
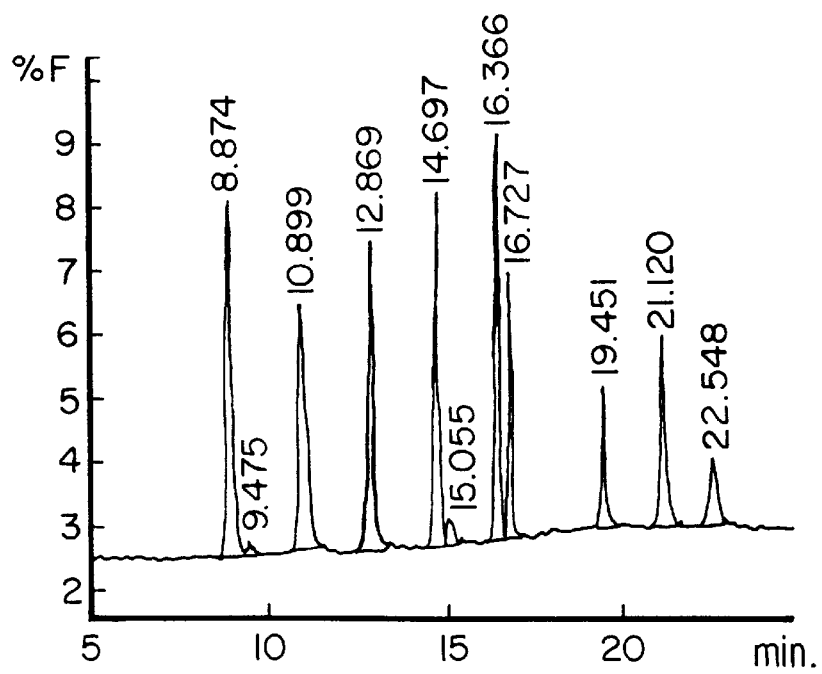

HPLC elution profiles of acid extracts from psoriatic scales revealed a major peak at 22.5 minutes for all 5 patients studied (FIG. 8a). The retention time of this peak corresponds to the retention time of protoporphyrin IX (FIG. 8b). A smaller peak, which did not match any of the porphyrin standards retention times, was present at 13.7 minutes in one patient.

EXAMPLE 2

Figure 9:
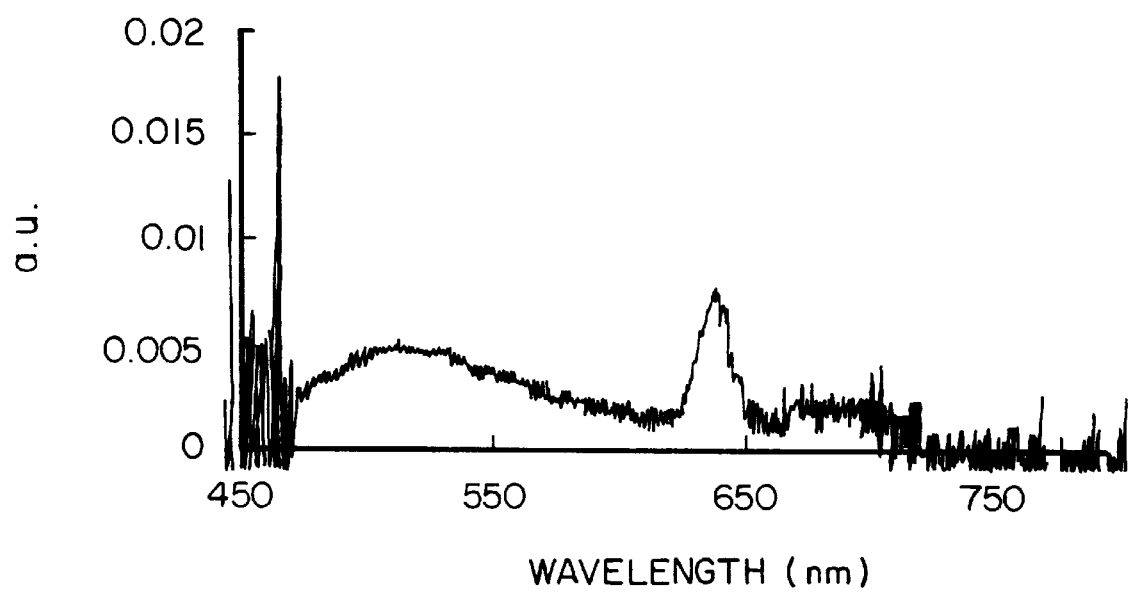
FIG. 9: Autofluorescence spectra from psoriatic plaque of the patient treated in Example 2, before treatment.

A patient was selected for treatment on the basis of having at least two psoriatic plaques of at least 5×5 cm located on the trunk or limbs with the presence of elevated endogenous porphyrin levels, as determined by in vivo spectrophotometry. The autofluorescence spectrum was recorded using a modified computerized fluorescence spectroanalyzer system (Zeng et al., 1993). The light source was a 442 nm He-Cd laser connected to an optical multi-channel analyzer (OMA) and a personal computer. The laser light reached the skin through an optical fiber equipped with a microlens. The emitted fluorescent light was collected with another optical fiber and transmitted to the OMA for spectral analysis. Presence of porphyrins in the skin was detected by a distinct 630–635 nm band in the red region of the fluorescence spectrum, as shown in FIG. 9.

A 150 Watt lamp equipped with a 400 nm long pass filter was used for light treatment of the patient to affect treatment with visible light and minimize exposure to ultraviolet light. The power output was measured with a light radiometer before each treatment. A zone of 3×3 cm psoriatic skin was exposed three times a week to visible light with exposure times starting at 1 minute, and increased by doubling the time until the treatment time reached 20 minutes. The treatment time remained constant at 20 minutes thereafter.

The patient received a total of 18 treatments (thrice weekly for 6 weeks). The light-treated psoriatic plaque was evaluated for disease characteristics using a quantitative method at weekly screening visits during treatment and one and three weeks after the last treatment. Autofluorescence spectra were also taken weekly.

The quantitative method for psoriatic plaque evaluation used a system of scoring the degree of erythema, scaling and elevation, as follows: erythema, 0-absent; 1 -light pink, 2-light/red pink, 3-red, 4-very red; scaling, 0-absent, 1-rare scale, 2-poorly defined scale, 3-defined scales, 4- heavy scale; elevation, 0-absent, 1-barely perceptible elevation, 2-slight elevation, 3-moderate elevation, 4-marked ridge.

Figure 10:
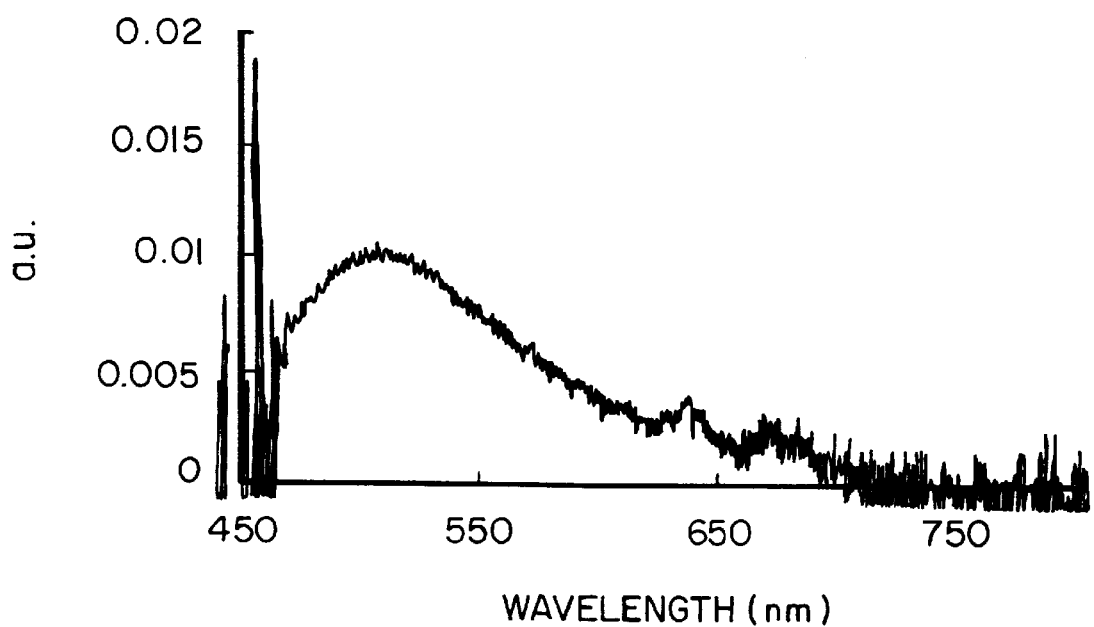
FIG. 10: Autofluorescence spectra of psoriatic plaque of patient treated in Example 2, after treatment.
Figure 11:
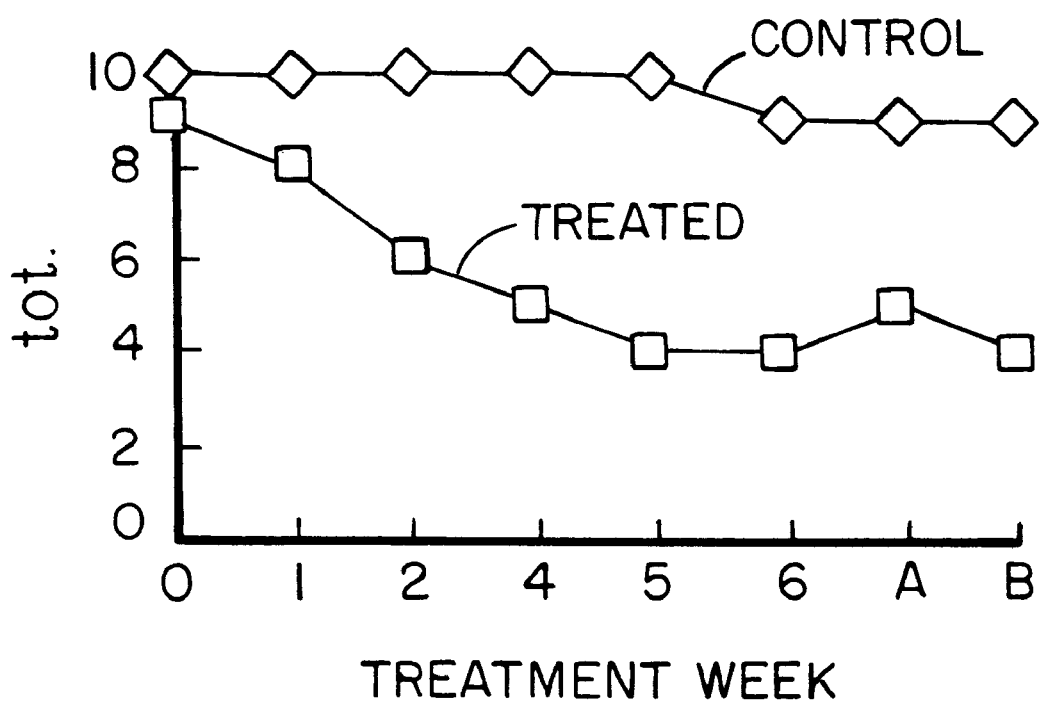
FIG. 11: Psoriatic plaque scores for patient treated in Example 2, over time with "A" and "B" representing follow-up visits one and three weeks after the last treatment.

Treatment with visible light resulted in the diminishing of the 630–635 nm Protoporphyrin IX peak in the plaque and the appearance of a new peak at around 670 nm, both immediately after treatment and over the course of the study. FIGS. 9 and 10 show the autofluorescence spectra before and after treatment with visible light. The patient responded well to the treatment and the treated area was significantly cleared of psoriasis, as reflected in the graph of FIG. 11 showing psoriatic plaque scores. The patient's area of treatment was approximately the size of the psoriatic plaque. The presence of the Protoporphyrin IX peak in the treated plaque disappeared over the course of treatment.

REFERENCES

The following documents are incorporated herein by reference.

Anderson, R. R. & Parrish, J. A. (1982), *Optical properties of human skin*. New York: Plenum. Arakane, K., Ryu, A., Hayashi, C., Masunaga, T., Shinmoto, K., Hannah, Mashiko, S., Nagano, T. & Hirobe, M. (1996). Singlet oxygen (1 delta g) generation from coproporphyrin in Propionibacterim acnes on irradiation. *Biochemical & Biophysical Research Communications*, 223:578–822.

Bech, O., Phillips, D., Moan, J. and MacRobert, A. J. (1997). A hydroxypyridinone (CP94) enhances protoporphyrin IX formation in 5-aminolaevulinc acid treated cells. J. of photochemistry and photobiology B: Biology 41:136–144.

Berg, K., Anholt, H., Bech, O. and Moan, J. (1996). The influence of iron chelators on accumulation of porotophyrin IX in 5-aminolaevulinc acid-treated cells. British Journal of Cancer 74:668–697.

Boehncke, W. H., Sterry, W. & Kaufmann, R. (1994). Treatment of psoriasis by topical photodynamic therapy with polychromatic light [letter]. *Lancet*, 343:801.

Bommer, S. (1927). Hautuntersuchungen im gefilterten quarzlicht. *Klin Wochenschrift*, 6;1142–1144.

Brault, D., Vever-bizet, C. and Doan, T. L. (1996). Spectrofluorimetric study of porphyrin incorporation into membrane models-evidence for pH effects. *biochimica et Biophysica ACTA* 857:238–250.

Chang, S., MacRobert, A. J., Porter, J. B. and Brown, S. (1997). The efficacy of an iron chelator (CP94) in increasing cellular portoporphyrin IX following intravesical 5-aminolaevulinic acid administration: an in vivo study. *J. of photochemistry and photobiology B: Biology* 38:114–122.

Cornelius, C. E. & Ludwig, G. D. (1967). Red fluorescence of comedones: production of porphyrins by Cornybacterium acnes. *Journal of Investigate Dermatology*, 49:368–370.

Dhingra, J. K., Perrault, D. F., Jr., McMillan, K., Rebeiz, E. E., Kabani, S., Manoharan, R., Itzkan, I., Feld, M. S. & Shapsay, S. M. (1966). Early diagnosis of upper aerodigestive tract cancer by autofluorescence. *Archives of Otolaryngology —Head & Neck Surgery*, 112:1181–6.

Fuchs, C., Riesenberg, R., Siegert, J. and Baumgartner, R. (1997). pH-dependent formation of 5-aminolaevulinc acid-induced portoporphyrin IX in fibrosarcoma cells. *J. of photochemistry and photobiology B:Biology* 40:49–54.

Ghadially, F. N. & Neish, W. J. P. (1960). Porphyrin fluorescence of experimentally produced squamous cell carcinoma. *Nature*, 188:1124.

Ghadially, F. N., Neish W. J. P., Dawkins H. C. (1963). Mechanisms involved in the production of red fluorescence of human and experimental tumors. *J. Path. Bactiol.* 85:77–92.

Goerz, G., Link-Mannhardt, A., Bolsen, K., Zumdick, M., Fritsch, C. & Schurer, N.Y. (1995). Porphyrin concentrations in various human tissues. *Experimental Dermatology*, 4:218–20.

Goff, B. A., Bachor, R., Kollias, N. & Hasan, T. (1992). Effects of photodynamic therapy with topical application of 5-aminolevulinic acid on normal skin of hairless guinea pigs. *Journal of Photochemistry & Photobiology. B - Biology*, 15:239–51.

Gog, H. v. & Schothorst, A. A. (1973). Determination of very small amounts of protoporphyrin in epidermis, plasma, and blister fluids. *Journal of Investigative Dermatology*, 61:42–5.

Gougerot, H. & Patte, A. (1939). Fluorescence des épithéliomas a la lumiere de Wood. *Bulletin de la société Francaise de Dermatologie et de Syphiligraphie*, 46:288–295.

Gudgin Dickson, E. F. & Pottier, R. H. (1995). On the role of protoporphyrin IX photoproducts in photodynamic therapy [news]. *Journal of Photochemistry & Photobiology, B - Biology*, 29:91–3.

Hanania, E. and Malik, Z. (1992). The effect of EDTA and Serum on endogenous porphyrin accumulation and photodynamic sensitization of human K562 lukemic cells. *Cancer letters* 65:127–131.

Harris, D. & Werkhaven, J. (1987). Endogenous porphyrin fluorescence in tumors. *Lasers in Surgery and Medicine* 7: 467–472.

Ingrams D. R. et al. (1997). Autofluorescence characteristics of oral mucosa. *Head & Neck*, January 1997:27.

Johnsson, A. et al. (1987). Fluorescence from pilosebaceous follicles. *Arch Dermatol Res* 279:190–193.

Kjeldstad, B., Johnsson, A. and Sandberg, S. (1984). Influence of pH on Porphyrin Production in Propionibacterium acnes. *Arch Dermatol Res* 276:396–400.

Konig, K., Dietel, W. & Schubert, H. (1989). In vivo autofluorescence investigations on animal tumors. *Neoplasma,* 36:135–8.

Konig et al. (1992). Fluorescence detection and photodynamic activity of endogenous protoporphyrin in human skin. *Optical Engineering* 31:(7) 1470. 3

Konig et al. (1994). In-vivo fluorescence detection and imaging of porphyrin-producing bacteria in the human skin and in the oral cavity for diagnosis of acne vulgaris, caries, and squamous cell carcinoma. *SPIE* 2135:129.

Lee, W. et al. (1978). Comparative studies of porphyrin production in Propionibacterium acnes and Propionibacterium granulosum. *J. Bacteriology* 133(2):811 .

Lohman, W. & Paul, E. 1988). In situ detection of melanomas by fluorescence measurement. *Naturwissenschaften,* 75:201–2.

Lucchina, L. et al. (1996). Fluorescence photography n the evaluation of acne. *J. Am Acad Dermatol* 35:58–63.

Lui, H., Zeng, H., McLean, D. I., MacAulay, C. E. & Palcic, B. (1996). In vivo fluorescence spectroscopy monitoring of BPD verteporfin concentration changes in skin tissue during photodynamic skin cancern. *Journal of Dermatological Science,* 12:87.

Malina, L. et al. (1978). Skin porphyrin assay in porphyrin. *Clinica Chimica Acta* 83:55–59.

McGinley, K. et al. (1980). Facial follicular porphyrin fluorescence: correlation with age and density of Propionibacterium acnes. *Journal of Dermatology* 102:437.

Nelson, L. S. et al. (1985). Tropical 5-aminolevulinic acid (ALA) for the photodynamic therapy of psoriasis and actinic keratoses. *Am. Soc. For Laser Medicine and Surgery Abstracts*, p. 43, Abstract 202.

Pathak, M. A. & Burnett, J. W. (1964). The porphyrin content of skin. *Journal of Investigative Dermatology,* 43:1190–20.

Policard, A. (1924). Etude sur les aspects offerts par des tumeurs experimentales examinees a la lumiere de Wood. *Comptes Rendus de la societe de biologie v.*91:423–24.

Rebeiz, N., Rebeiz, C., Arkins, S., Kelley, Q. and Rebeiz, C. A. (1992). Photodestruction of tumor cells by induction of endogenous accumulation of portoporphyrin IX; enhancement by 1, 10-phena and throline. *Photochemistry and Photobiology* 55 (3):531–435.

Rhodes, L. E., Tsoukas, M. M., Anderson, R. R. & Kollias, N. (1997). Iontophoretic Delivery of Ala Provides a Quantitative Model for Ala Pharmacokinetics and Ppix Phototoxicity in Human Skin. *Journal of Investigative Dermatology,* 108:87–91.

Rochese, F. (1954). The fluorescence of cancer under the Wood's light. *Oral Surg Med Oral Pathol,* 7:967–971.

Sterenborg, H., Saarnak, A. E., Frank, R. & Motamedi, M. (1996). Evaluation of Spectral Correction Techniques for Fluorescence Measurements On Pigmented Lesions in Vivo. *Journal of Photochemistry & Photobiology, B - Biology,* 35:159–165.

Stringer, M. R., Collins, P., Robinson, D. J., Stables, G. I. & Sheehandare, R. A. (1996). The accumulation of Protoporphyrin Ix in Plaque Psoriasis After Topical Application of 5-Aminolevulinic Acid Indicated a Potential For superficial Photodynamic Therapy. *Journal of Investigative Dermatology,* 107:76–81.

Szeimies, R., Calzavara-Pinton, P., Karrer, S., Ortel, B. and Landthaler, M. (1996). Topical photodynamic therapy in dermatology. *J. of photochemistry and photobiology* 36:213–219.

Tan, W. C., Krasner, N., O'Toole, P. and Lombard, M. (1997). Enhancement of photodynamic therapy in gastric cancer cells by removal of iron. Gut 41:14–18.

Zeng, H. et al. (1993a). Laser-induced changes in autofluorescence of in vivo skin. SPIE 1882 *Laser-Tissue Interaction IV:* 278.

Zeng. H., MacAulay, C., McLean, D. and Palcic, B. (1993b). Novel microspectrophotometer and its biomedical applications. *Optical Engineering* 32(8):1809–1814.

Zeng, H. et al. (1995). Spectroscopic and Microscopic characteristics of human skin autofluorescence emission. *Phtochemistry and Photobiology* 61(6) 639.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of treating psoriasis comprising:
   a. identifying a psoriatic plaque with elevated endogenous porphyrin levels;
   b. treating the psoriatic plaque with visible light.

2. The method of claim 1, wherein the step of identifying the psoriatic plaque comprises illuminating the plaque with excitatory light and detecting autofluorecent light from the plaque.

3. The method of claim 2, wherein the autofluorescent light comprises red light.

4. The method of claim 2 further comprising spectrophotometric analysis of the autofluorescent light to detect a fluorescent emission peak of a porphyrin.

5. The method of claim 4 wherein the fluorescent emission peak is at about 630–635 nm.

6. The method of claim 1 wherein the visible light comprises blue light.

7. The method of claim 2 wherein the visible light comprises blue light.

8. The method of claim 6 wherein the visible light comprises light having a wavelength longer than about 400 nm.

9. The method of claim 2 wherein the excitatory light comprises light having a wavelength between about 320 nm and about 500 nm.

10. The method of claim 9 wherein the excitatory light comprises light having a wavelength between about 400 nm and 500 nm.

11. The method of claim 1 further comprising elevating endogenous porphyrin levels in the psoriatic plaque by buffering the pH in the plaque.

12. The method of claim 11 further comprising administering a topical composition to the plaque which buffers the pH of at least a portion of the plaque at a pH of about 5.7 to about 6.5.

13. The method of claim 1 further comprising the step of administering a topical composition comprising an iron chelator to the plaque.

14. The method of claim 13 wherein the iron chelator is selected from the group consisting of CP94, EDTA and desferrioxamine.

15. A diagnostic method for identifying a psoriatic plaque susceptible to treatment with visible light and having an elevated porphyrin level, comprising illuminating the plaque with excitatory light and detecting autofluorescent light from the plaque.

16. The diagnostic method of claim 15, wherein the autofluorescent light comprises red light.

17. The method of claim 15 further comprising spectrophotometric analysis of the autofluorescent light to detect a fluorescent emission peak at about 630 nm to about 635 nm.

18. The method of claim 15 wherein the visible light comprises light having a wavelength longer than about 400 nm.

19. The method of claim 15 wherein the excitatory light comprises light having a wavelength longer than about 400 nm and about 500 nm.

* * * * *